United States Patent
Cowin et al.

(10) Patent No.: US 8,574,571 B2
(45) Date of Patent: Nov. 5, 2013

(54) METHODS AND COMPOSITIONS FOR MODULATING WOUND REPAIR

(75) Inventors: Allison June Cowin, Beaumont (AU); Hugh Douglas Campbell, Fraser (AU); Barry Powell, Erindale (AU)

(73) Assignees: Womens & Childrens Health Research Institute (AU); Adelaide Research & Innovation Pty Ltd (AU); The Australian National University (AU)

( * ) Notice: Subject to any disclaimer, the term of this patent is extended or adjusted under 35 U.S.C. 154(b) by 981 days.

(21) Appl. No.: 12/091,146

(22) PCT Filed: Oct. 25, 2006

(86) PCT No.: PCT/AU2006/001610
§ 371 (c)(1),
(2), (4) Date: Sep. 23, 2008

(87) PCT Pub. No.: WO2007/048202
PCT Pub. Date: May 3, 2007

(65) Prior Publication Data
US 2010/0203064 A1  Aug. 12, 2010

(30) Foreign Application Priority Data

Oct. 25, 2005  (AU) ............................... 2005905891
Sep. 18, 2006  (AU) ............................... 2006905128

(51) Int. Cl.
*A61K 39/395* (2006.01)

(52) U.S. Cl.
USPC ..................................... 424/130.1; 424/145.1

(58) Field of Classification Search
None
See application file for complete search history.

(56) References Cited

U.S. PATENT DOCUMENTS

| 5,484,596 A * | 1/1996 | Hanna et al. ............... 424/277.1 |
| 5,662,904 A   | 9/1997 | Ferguson et al. |
| 6,713,059 B2 * | 3/2004 | Kende et al. ............... 424/150.1 |
| 7,566,446 B2 * | 7/2009 | Ferguson et al. .......... 424/78.06 |

FOREIGN PATENT DOCUMENTS

| WO | WO 98/24465 | 6/1998 |
| WO | WO 99/41364 | 8/1999 |

OTHER PUBLICATIONS

Kopecki et al. Topically Applied Flightless I Neutralizing Antibodies Improve Healing of Blistered Skin in a Murine Model of Epidermolysis Bullosa Acquisita. Journal of Investigative Dermatology (2013) 133, 1008-1016.*
Jackson JE, Kopecki Z, Adams DH et al. (2012) Flii neutralising antibodies improve wound healing and reduce scar formation in porcine pre-clinical studies. Wound Repair Regen 20:523-36.*
Adams et al. Attenuation of Flightless I, an actin-remodelling protein, improves burn injury repair via modulation of transforming growth factor (TGF)-beta1 and TGF-beta3. Br J Dermatol 161:326-36, 2009.*
Shah, M. et al. "Neutralising Antibody to TGF-Beta 1, 2 Reduces Cutaneous Scarring in Adult Rodents" Journal of Cell Science, Cambridge University Press, London, GB, vol. 107, Jan. 1, 1994, pp. 1137-1157, XP000609040 ISSN: 0021-9533 *the whole document* (21 pages).
Cowin, Allison J., et al. "Differential Effect of Wounding on Actin and its Associated Proteins, Paxillin and Gelsolin, in Fetal Skin Explants"; Journal of Investigative Dermatology, Nature Publishing Group, DB, vol. 120, No. 6, Jun. 1, 2003, pp. 1118-1129, XP009125901 ISSN: 0022-202X *pp. 1127-1128* (12 pages).
Kubo Masahide, et al. "Persistent Down-Regulation of Fli1, a Suppressor of Collagen Transcription, in Fibrotic Scleroderma Skin"; American Journal of Pathology, American Society for Investigative Pathology, US, vol. 163, No. 2, Aug. 1, 2003, pp. 571-581, XP009126142 ISSN: 0002-9440 *the whole document* (12 pages).
Cowin, A.J., et al. "Flightless I Deficiency Enhances Wound repair by Increasing Cell Migration and Proliferation" Apr. 2007, The Journal of Pathology Apr. 2007, vol. 211, Nr. 5, pp. 572-581, XP002557307 ISSN: 0022-3417 *the whole document* (10 pages).
Supplementary European Search Report Issued by the European Patent Office on Nov. 25, 2009 in corresponding European Application EP 06 79 0437, (12 pages).
Davy DA et al. "The flightless I protein colocalizes with actin- and microtubule-based structures in motile Swiss 3T3 fibroblasts: evidence for the involvement of PI 3-kinase and Ras-related small GTPases." J Cell Sci. Feb. 2001; 114(Pt 3):549-62. (Abstract; p. 558 right column last paragraph; p. 559 right column last paragraph; Materials and Methods).
Czuwara-Ladykowska J. et al. "Fli-1 inhibits collagen type I production in dermal fibroblasts via an Sp1-dependent pathway." J Biol Chem. Jun. 15, 2001; 276(24):20839-48. (Abstract; p. 20848 left column first paragraph).

* cited by examiner

*Primary Examiner* — Maher Haddad
(74) *Attorney, Agent, or Firm* — Hovey Williams LLP

(57) ABSTRACT

The present invention relates to a method of modulating repair of a wound. The method includes modulating expression and/or activity of Flightless I in cells involved in repair of the wound.

9 Claims, 12 Drawing Sheets

METHODS AND COMPOSITIONS FOR MODULATING WOUND REPAIR

This application claims priority from and the benefit of Australian patent application Nos. 2005905891 and 2006905128 filed on 25 Oct. 2005 and 18 Sep. 2006, respectively, the disclosures of which are incorporated herein by reference.

FIELD OF THE INVENTION

The present invention relates to methods and compositions for modulating wound repair and scar formation.

The present invention also relates to methods and compositions for preventing and/or treating diseases, conditions and states associated with undesired or abnormal fibrosis, and to methods and compositions for modulating migration and/or proliferation of cells involved in wound repair, scar formation or fibrosis.

The present invention further relates to isolated skin cells with altered expression of a regulator of wound repair.

BACKGROUND OF THE INVENTION

Wound healing is a complex and dynamic process that results in the restoration of cellular structures and tissue layers. Generally, the wound healing process can be divided into 3 distinct phases: the inflammatory phase, the proliferative phase, and the remodeling phase. Each of these phases involves a complex and coordinated series of events that includes chemotaxis, phagocytosis, neocollagenesis, collagen degradation, and collagen remodeling.

The recruitment of a variety of specialised cell types to the site of a wound is also a critical part of the process of wound healing. This process requires extracellular matrix and basement membrane deposition, angiogenesis, selective protease activity and re-epithelialisation.

One component of the healing process in mammals is the stimulation of fibroblasts to generate the extracellular matrix. This extracellular matrix constitutes a major component of the connective tissue that develops to repair the wound area.

The actin cytoskeleton is an essential network of filaments found in all cells. Reorganisation of the actin cytoskeleton is central to changes in cell adhesion and motility that underpin wound repair processes. These changes include the lammellipodial crawling of keratinocytes during wound re-epithelialisation, infiltration of inflammatory cells and migration of fibroblasts required for the deposition and remodelling of the extracellular matrix and dermal contraction at the wound site.

Many regulatory proteins influence actin assembly and organisation. For example, members of the gelsolin family of proteins appear to regulate actin filaments by severing pre-existing filaments and/or capping the filament ends. After severing, the proteins remain attached to the "barbed" ends of the broken filament, thereby preventing annealing or addition of actin monomers. Actin filaments are subsequently uncapped by interaction with phosphoinositides, leading to rapid actin assembly. This is the first step in enabling cells to reorientate their cytoskeleton to drive changes in motility, adhesion and contraction.

There is a continuing need to develop methods and medicaments that promote the healing of wounds. For example, it is often desirable to increase the rate of healing in the case of acute wounds (such as penetrative injuries, burns, nerve damage and wounds resulting from elective surgery), chronic wounds (such as diabetic, venous and decubitus ulceration) or for healing wounds in individuals with compromised wound healing capacity, such as the elderly.

However, where the rate of wound healing is increased, there is often an associated increase in scar formation. In most cases, an increase in scar formation is often of secondary importance as compared to the desired increase in the rate of healing. However, there are often instances where the regulation of scar formation is of primary importance and the rate of wound healing is only of secondary consideration. Examples of such situations are scars of the skin where excessive scarring may be detrimental to tissue function and particularly when scar contracture occurs (for instance skin burns and wounds which impair flexibility of a joint). The reduction of scarring to the skin when cosmetic considerations are important is also highly desirable.

There are also a number of diseases, conditions and states in which internal scarring or fibrosis can be highly detrimental. Fibrotic disorders are characterised by the accumulation of fibrous tissue (predominately collagens) in an abnormal fashion within the tissue. Accumulation of such fibrous tissues may result from a variety of disease processes.

Current treatments for wound healing include pressure garments, silicone dressings, and hydrocortisone injections. However, these treatments are empirical, unreliable and unpredictable. There are also no prescription drugs available for the treatment of dermal scarring.

Accordingly, there remains a need to develop new agents and therapeutic strategies that may be used to modulate the healing of wounds, scarring and fibrosis. The present invention arises from the identification that Flightless I, a member of the gelsolin family, is an important mediator of wound repair, and that repair of a wound may be modulated by modulating the activity and/or expression of this protein.

A reference herein to a patent document or other matter which is given as prior art is not to be taken as an admission that that document or matter was, in Australia or any other country, known or that the information it contains was part of the common general knowledge as at the priority date of any of the claims.

SUMMARY OF THE INVENTION

The present invention arises out of studies into the role of the Flightless I protein in wound repair. The present studies demonstrate that modulating the activity of Flightless I regulates wound healing. As such, Flightless I is a target for manipulation to improve wound healing and scar formation, and to prevent and/or treat fibrotic disorders.

Accordingly, in one embodiment the present invention provides a method of modulating repair of a wound, the method including modulating expression and/or activity of Flightless I in cells involved in repair of the wound.

The present invention also provides use of an agent that modulates expression and/or activity of Flightless I in the preparation of a medicament for modulating wound repair.

The present invention also provides a pharmaceutical composition when used to modulate repair of a wound, the composition including an effective amount of an agent that modulates expression and/or activity of Flightless I.

The present invention also provides a method of modulating scar formation in a wound of a subject, the method including the step of delivering to the wound an effective amount of an agent that modulates expression and/or activity of Flightless I.

The present invention also provides use of an agent that modulates expression and/or activity of Flightless I in the preparation of a medicament for modulating scar formation.

The present invention also provides a pharmaceutical composition when used to modulate scar formation, the composition including an effective amount of an agent that modulates expression and/or activity of Flightless I.

The present invention also provides a method of preventing and/or treating a disease, condition or state associated with undesired or abnormal fibrosis in a subject, the method including the step of administering to the subject a therapeutically effective amount of an agent that modulates expression and/or activity of Flightless I.

The present invention also provides use of an agent that modulates expression and/or activity of Flightless I in the preparation of a medicament for preventing and/or treating a disease, condition or state associated with undesired or abnormal fibrosis.

The present invention also provides a pharmaceutical composition when used to prevent and/or treat a disease, condition or state associated with undesired or abnormal fibrosis, the composition including an effective amount of an agent that modulates expression and/or activity of Flightless I.

The present invention also provides a method of modulating one or more of expression, secretion and/or activity of TGF-β and/or collagen, the method including the step of modulating expression and/or activity of Flightless I in a cell.

The present invention also provides use of an agent that modulates the expression and/or activity of Flightless I in the preparation of a medicament for modulating one or more of expression, secretion and/or activity of TGF-β and/or collagen.

The present invention also provides a pharmaceutical composition when used to modulate one or more of expression, secretion and/or activity of TGF-β and/or collagen, the composition including an effective amount of an agent that modulates expression and/or activity of Flightless I.

The present invention also provides use of an agent that modulates expression and/or activity of Flightless I in the preparation of a medicament for modulating wound repair.

The present invention also provides a method of modulating migration and/or proliferation of a cell involved in wound repair, scar formation or fibrosis, the method including the step of modulating the expression and/or activity of Flightless I in the cell.

The present invention also provides use of an agent that modulates the expression and/or activity of Flightless I in the preparation of a medicament for modulating migration and/or proliferation of a cell involved in wound repair, scar formation or fibrosis.

The present invention also provides a pharmaceutical composition when used to modulate migration and/or proliferation of a cell involved in wound repair, scar formation or fibrosis, the composition including an effective amount of an agent that modulates expression and/or activity of Flightless I.

The present invention also provides an isolated skin cell, or a progenitor or derivative thereof, the cell having an altered expression and/or activity of Flightless I.

The present invention also provides an isolated skin cell, or a progenitor or derivative thereof, the cell including a nucleic acid that modulates Flightless I expression and/or activity in the cell.

Various terms that will be used throughout the specification have meanings that will be well understood by a skilled addressee. However, for ease of reference, some of these terms will now be defined.

The term "Flightless I" as used throughout the specification will be understood to mean a protein with at least 50% sequence identity to human Flightless I. A Flightless I protein may be identified, for example, by the BLAST algorithm, as described in Altschul et al. (1990) *J. Mol. Biol.* 215:403-410.

The term "modulate" as used throughout the specification is to be understood to mean a promotion or inhibition of a process.

In this regard, it will be appreciated that depending upon the characteristics of the particular biological system, an increase in rate and/or extent of wound repair, for example, may result from either an increase or decrease in the expression and/or activity of Flightless I. For the same reason, an inhibition in rate and/or extent of wound repair may also result from either an increase or decrease in the expression and/or activity of Flightless I. A similar situation applies to the case of modulating the rate and/or extent of scar formation, and the modulation of proliferation and/or migration of cells involved in wound healing.

It will also be appreciated that the modulation of Flightless I expression and/or activity in cells involved in repair (healing) of a wound, or in cells involved in scar formation, is a modulation of the expression and/or activity in one or more cells involved in these processes, directly or indirectly, and includes cell types such as fibroblasts, keratinocytes, endothelial cells, neutrophils, macrophages, and other inflammatory cells.

It will be further appreciated that the modulation of the expression and/or activity of Flightless I includes within its scope one or more of a modulation of the Flightless I protein level, an alteration in the activity of the Flightless I protein, an alteration in the intracellular and/or extracellular localisation of the protein, and an alteration in the rate or level of secretion of the protein from a cell.

The term "biological system" as used throughout the specification is to be understood to mean any multi-cellular system and includes isolated groups of cells to whole organisms.

The term "variant" as used throughout the specification is to be understood to mean an amino acid sequence of a polypeptide or protein that is altered by one or more amino acids. The variant may have "conservative" changes, wherein a substituted amino acid has similar structural or chemical properties to the replaced amino acid (e.g., replacement of leucine with isoleucine). A variant may also have "non-conservative" changes (e.g., replacement of a glycine with a tryptophan) or a deletion and/or insertion of one or more amino acids.

The term "nucleic acid" as used throughout the specification is to be understood to mean any oligonucleotide or polynucleotide. The nucleic acid may be DNA or RNA and may be single stranded or double stranded. The nucleic acid may be any type of nucleic acid, including a nucleic acid of genomic origin, cDNA origin (ie derived from a mRNA), derived from a virus, or of synthetic origin.

In this regard, an oligonucleotide or polynucleotide may be modified at the base moiety, sugar moiety, or phosphate backbone, and may include other appending groups to facilitate the function of the nucleic acid. The oligonucleotide or polynucleotide may be modified at any position on its structure with constituents generally known in the art. For example, an oligonucleotide may include at least one modified base moiety which is selected from the group including 5-fluorouracil, 5-bromouracil, 5-chlorouracil, 5-iodouracil, hypoxanthine, xanthine, 4-acetylcytosine, 5-(carboxyliydroxylmethyl) uracil,5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta D-mannosylqueosine, 5'-methoxycarboxymethyluracil, 5-methoxyuracil, 2-methylthio-N6-isopentenyladenine, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil5-oxyacetic acid methylester, uracil-5-oxyacetic acid, 5-methyl-2-thiouracil, 3-(3-amino-3-N-2-carboxypropyl) uracil, and 2,6-diaminopurine.

The oligonucleotide or polynucleotide may also include at least one modified sugar moiety selected from the group including, but not limited to, arabinose, 2-fluoroarabinose, xylulose, and hexose. In addition, the oligonucleotide or polynucleotide may include at least one modified phosphate backbone, such as a phosphorothioate, a phosphorodithioate, a phosphoramidothioate, a phosphoramidate, a phosphordiamidate, a methylphosphonate, an alkyl phosphotriester, and a formacetal or any analogue thereof.

The term "subject" as used throughout the specification is to be understood to mean any multicellular organism, including an animal or human subject. For example, the subject may be a human or other mammal, a primate, a livestock animal (eg. a horse, a cow, a sheep, a pig, or a goat), a companion animal (eg. a dog, cat), a laboratory test animal (eg. a mouse, a rat, a guinea pig, a bird), an animal of veterinary significance, or an animal of economic significance.

The term "isolated" as used throughout the specification is to be understood to mean that a material is removed from its original environment, such as removed from its natural environment if it is naturally-occurring. For example, a naturally-occurring polynucleotide, polypeptide or cell present in a living animal is not isolated, but the same polynucleotide, polypeptide or cell separated from some or all of the coexisting materials in the natural system, is isolated, even if subsequently reintroduced into the natural system.

GENERAL DESCRIPTION OF THE INVENTION

Figure 1:
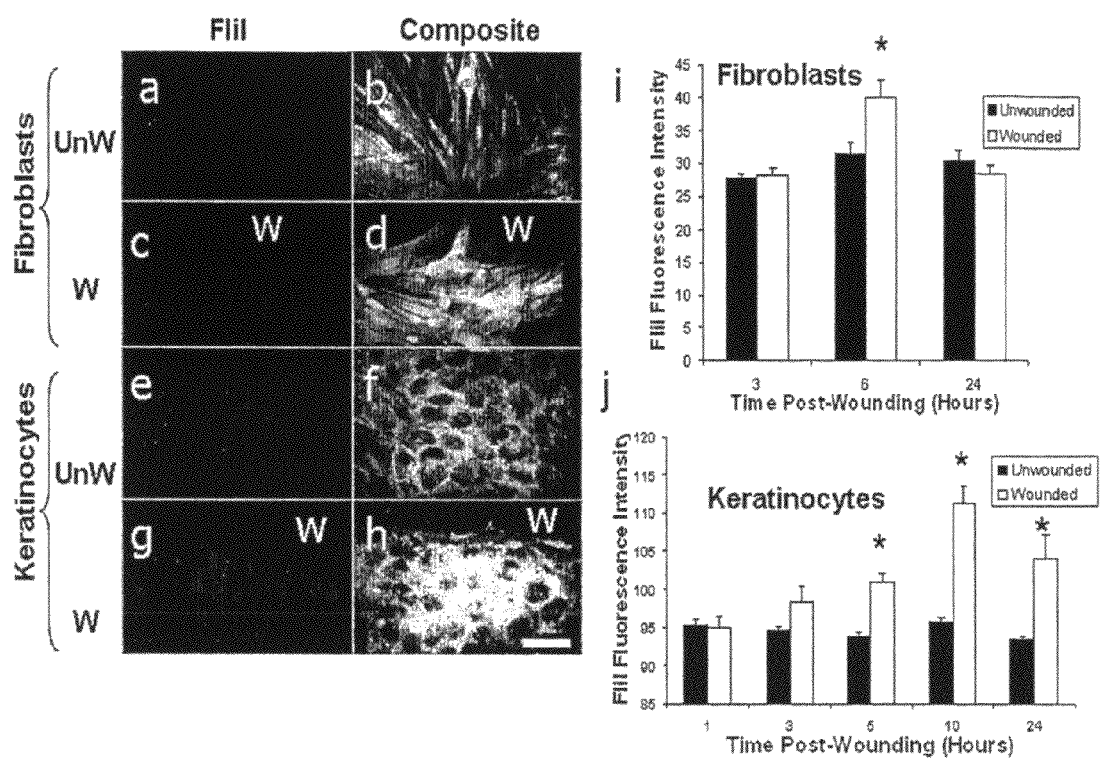
FIG. 1 shows that wounding upregulates FliI expression in human fibroblasts and keratinocytes. Confluent human fibroblasts and keratinocytes (HaCaTs) were scratch-wounded and stained for FliI and actin by immunocytochemistry. Representative images are shown. (a) Unwounded (UnW) fibroblasts stained for FliI (red), (b) composite of FliI and actin (green). Colocalisation of FliI and actin is shown as yellow. (c) Wounded (W) fibroblasts 6 hours post-wounding stained for FliI (red), (d) composite of FliI and actin (green). (e) Unwounded keratinocytes stained for FliI (red), (f) composite of FliI and actin (green). (g) Wounded keratinocytes at 10 hours post-wounding stained for FliI (red), (h) composite of FliI and actin (green). (i) and (j) Integrated fluorescence intensity was determined for fibroblasts and keratinocytes using AnalySIS software package. Results represent mean+/−s.e.m. (n=6 for each group, *in I refers to P=0.010, *in J refers to P=0.025). Bar in h=50 µm and refers to all images.

As discussed above, in one embodiment the present invention provides a method of modulating repair of a wound, the method including modulating expression and/or activity of Flightless I in cells involved in repair of the wound.

This present invention may be used to promote or inhibit the repair of healing of a wound present in a biological system. For example, the present invention may be used to repair a wound in vivo, such as a wound in an entire human or animal subject.

In this regard, the term "biological system" as used in the various relevant embodiments of the present invention is to be understood to mean a multi-cellular system, and includes isolated groups of cells to whole organisms. For example, the biological system may be a tissue or organ, or an entire human or animal subject.

It will be appreciated however that the present invention may also be used to modulate wound healing of cells in vitro.

The term "Flightless I" as used throughout the specification in the various embodiments of the present invention will be understood to mean a protein with at least 50% sequence identity to human Flightless I. A Flightless I protein may be identified, for example, by the BLAST algorithm which identifies local alignments between the sequences in the database and predicts the probability of the local alignment occurring by chance. The BLAST algorithm is as described in Altschul et al. (1990) *J. Mol. Biol.* 215:403-410.

Flightless I is a member of the gelsolin family. The human homologue of the Flightless I gene encodes a 140 kD protein, originally identified in *Drosophila* where mutations in the gene cause defects in the flight muscles which, consequently, are unable to support flight. The Flightless I protein is highly conserved between the mouse and human, and is the most evolutionarily conserved member of the gelsolin family, suggesting that it carries out important, conserved functions.

The amino acid sequence of the human form of Flightless I is provided in Genbank Accession No. NP_002009. The nucleotide sequence of the mRNA is provided in GenBank Accession No. NM_002018.

As discussed previously herein, the present invention may be used to promote or inhibit repair of a wound.

Examples of wounds include acute wounds (such as penetrative injuries, burns, nerve damage and wounds resulting from elective surgery), chronic wounds (such is diabetic, venous and decubitus ulceration) or wounds in individuals with compromised wound healing capacity, such as the elderly.

In one embodiment, repair of the wound is promoted. In this case, the expression and/or activity of Flightless I in cells involved in repair of the wound may be decreased.

In another embodiment, repair of the wound is inhibited. In this case, the expression and/or activity of Flightless I in the cells involved in repair of the wound may be increased.

However, it will also be appreciated that depending upon the characteristics of the particular biological system, an increase in rate and/or extent of wound repair, for example, may result from either an increase or decrease in the expression and/or activity of Flightless I. For the same reason, an inhibition in rate and/or extent of wound repair may also result from either an increase or decrease in the expression and/or activity of Flightless I.

For example, in the case of modulating repair of wounds such as burns, it may be that a increase in Flightless I activity may be associated with improved healing.

Methods for assessing the rate and extent of wound repair or healing are known in the art.

The present invention involves the modulation of the expression and/or activity of Flightless I in cells involved in repair of a wound. In one embodiment, the cells involved in repair of the wound are fibroblast cells or keratinocytes.

The modulation of one or more of the expression, secretion and/or activity of the Flightless I protein in the various embodiments of the present invention may be accomplished by a suitable method.

In one embodiment, the modulation of Flightless I expression and/or activity includes delivering or exposing to the cells involved in repair of the wound an effective amount of an agent that modulates expression and/or activity of Flightless I.

In this regard, it will be appreciated that the agent may modulate the expression and/or activity of the Flightless I protein directly or indirectly.

In one embodiment, the agent is delivered to a wound in a subject to modulate repair of the wound. For example, the agent may be applied to the wound directly and/or injected intradermally around the wound.

Accordingly, in another embodiment the present invention provides a method modulating repair of a wound in a subject, the method including delivering to the wound an effective amount of an agent that modulates expression and/or activity of Flightless I in cells involved in repair of the wound.

The subject may be, for example, a human or an animal subject, including a mammalian subject, a primate, a livestock animal (eg. a horse, a cow, a sheep, a pig, or a goat), a companion animal (eg. a dog, cat), a laboratory test animal (eg. a mouse, a rat, a guinea pig, a bird), an animal of veterinary significance, or an animal of economic significance.

In this regard, it will be understood that the modulation of expression and/or activity of Flightless I may occur at any one or more of prior to, concurrently with, and/or after a wound has occurred. Thus, the present invention not only contemplates the modulation of the expression and/or activity of Flightless I for the treatment of wounds after wounding has occurred, the present invention also contemplates modulation of the expression and/or activity of Flightless I before wounding has occurred.

Accordingly, the subject in the various embodiments of the present invention may be a subject suffering from a wound in need of repair, or alternatively, be a subject susceptible to wounding.

Examples of agents that may be used to modulate the expression and/or activity of Flightless I in the various embodiments of the present invention include a drug, a small molecule, a nucleic acid, an oligonucleotide, an oligopeptide, a polypeptide, a protein, an enzyme, a polysaccharide, a glycoprotein, a hormone, a receptor, a ligand for a receptor, a co-factor, an antisense oligonucleotide, a ribozyme, a small interfering RNA, a microRNA, a lipid, an aptamer, a virus, and an antibody or an antigen binding part thereof.

In one embodiment, the agent may increase the expression and/or activity of Flightless I. Agents that may increase the expression and/or activity of Flightless I are as previously discussed herein, and include agents such as a nucleic acid encoding a functional part of the Flightless I protein, agents that activate transcription of the Flightless I gene, or the Flightless I protein itself (or a variant or active fragment thereof). Such agents may be used to reduce or inhibit repair of a wound, or to reduce the extent of scar formation associated with the repair of a wound.

Methods for introducing agents into a cell are known in the art. The therapeutic delivery of biomolecules is generally as described in Bladon, C. (2002) "Pharmaceutical Chemistry: Therapeutic Aspects of Biomolecules" John Wiley & Sons Ltd.

For example, methods for introducing exogenous DNAs into cells are as described in Sambrook, J, Fritsch, E. F. and Maniatis, T. Molecular Cloning: A Laboratory Manual 2nd. ed. Cold Spring Harbor Laboratory Press, New York. (1989).

In an alternative embodiment, the agent may decrease the expression and/or activity of Flightless I.

A decrease in the expression and/or activity of Flightless I may be achieved by a suitable method.

For example, a decrease in expression may be accomplished by the use of one or more of a neutralizing antibody (or an antigen binding part thereof), use of an antisense nucleic acid that binds to the mRNA and which interferes with translation, the use of a molecule that can specifically repress transcription of an endogenous mRNA such as a specific DNA or RNA binding protein, a nucleic acid capable of forming a triple helix structure, a small interfering RNA, a microRNA, a ribozyme that can cleave a specific mRNA, or an inhibitory agent that interacts with Flightless I (or a regulator of Flightless I). Such agents may be used to promote or increase repair of a wound.

In one embodiment, the agent that decreases the expression and/or activity of Flightless I is a neutralising antibody (or an antigen binding part thereof), including a neutralising antibody to Flightless I (or an antigen binding part thereof).

The term "antigen binding part" is to be understood to mean the antigen-binding portion of an antibody molecule, including a Fab, Fab', F(ab')$_2$, Fv, a single-chain antibody (scFv), a chimeric antibody, a diabody or any polypeptide that contains at least a portion of an immunoglobulin that is sufficient to confer specific antigen binding, such as a molecule including one or more CDRs.

In one embodiment, the neutralising antibody to Flightless I is an antibody that binds specifically to the leucine rich repeat domain of the Flightless I protein. Methods for producing antibodies, including methods for producing neutralising antibodies, are known in the art, for example as described in Antibodies: A Laboratory Manual (1988) by Ed Harlow and David Lane, Cold Spring Harbor Laboratory Press, Cold Spring Harbor, N.Y.

In the case of antisense nucleic acids, these may be produced by a suitable method known in the art, including expression from a recombinant nucleic acid or by chemical synthesis. For example, phosphorothioate oligonucleotides may be synthesized by the method as described in Stein et al. (1988) *Nucl. Acids Res.* 16: 3209.

In the case of small interfering RNAs, these may be produced by a method known in the art. For example, methods of designing and using siRNAs to decrease the expression are essentially as described in Elbashir et al. (2001) *Nature* 411: 494-498, Harborth et al (2003) *Antisense Nucleic Acid Drug Dev.* 13: 83-106, and Semizarov et al (2003) *Proc Natl Acad Sci USA* 100: 6347-6352.

In the case of ribozymes, the functional constraints necessary for a nucleic acid to act as a ribozyme are essentially as described in Haseloff et al. (1988) *Nature* 334: 585-591; Koizumi et al., (1988) *FEBS Lett.* 228: 228-230; Koizumi et al., (1988) FEBS Lett. 239: 285-288). Ribozyme methods that involve inducing expression in a cell of ribozyme molecules are essentially as described in Grassi and Marini (1996) *Annals of Medicine* 28: 499-510; Gibson (1996) *Cancer and Metastasis Reviews* 15: 287-299.

The mechanism of ribozyme action involves sequence-specific hybridization of the ribozyme molecule to complementary target RNA, followed by endonucleolytic cleavage. Examples of ribozymes which may be used include engineered hammerhead motif ribozyme molecules that can specifically and efficiently catalyze endonucleolytic cleavage of sequences encoding the target sequence.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays, as known in the art.

In the case of an antibody, the antibody in the various embodiments of the present invention may be a polyclonal antibody, a monoclonal antibody, a chimeric antibody, a single chain antibody, a Fab fragment, and fragments produced by a Fab expression library.

For the production of antibodies, various hosts including goats, rabbits, rats, mice, humans, and others, may be immunized by injection with the polypeptide or any fragment or oligopeptide thereof that has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol.

Monoclonal antibodies may be prepared using any technique which provides for the production of antibody molecules by continuous cell lines in culture. These include, but are not limited to, the hybridoma technique, the human B-cell hybridoma technique, and the EBV-hybridoma technique (essentially as described in Kohler, G. et al. (1975) *Nature* 256: 495-497; Kozbor, D. et al. (1985) *J. Immunol. Methods* 81:31-42; Cote, R. J. et al. (1983) *Proc. Natl. Acad. Sci.* 80:2026-2030; Cole, S. P. et al. (1984) *Mol. Cell Biol.* 62:109-120).

Antibody fragments which contain specific binding sites may also be generated. For example, such fragments include $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (for example as described in Huse, W. D. et al. (1989) *Science* 254:1275-1281).

For example, a neutralising antibody to Flightless I may be produced by immunizing an animal against the leucine rich repeat domain of the protein. Various features of the Flightless I protein may be found in UniProtKB/Swiss-Prot entry Q13045.

The agent in the various embodiments of the present invention may also cause an alteration in the intracellular and/or extracellular localisation of Flightless I. For example, the agent may cause re-localisation of Flightless I from the cytoplasm of the cell to the nucleus of the cell, or re-localisation of Flightless I from the nucleus to the cytoplasm.

The agent in the various embodiments of the present invention may also modulate one or more of the expression, secretion, localisation and/or activity of a molecule upstream and/or downstream of Flightless I that is involved in wound repair. For example, the agent may modulate one or more of the expression, secretion and activity of a TGF-β protein, and/or modulate one or more of the expression, secretion and/or activity of collagen.

In this regard, TGF-β is a group of multifunctional proteins that control proliferation, differentiation, and other functions in many cell types. Members of the TGF-β family include TGF-β1, TGF-β2, and TGF-β3. The proteins all function through the same receptor signalling systems. Methods for identifying TGF-β proteins are known in the art.

In this regard, the term "TGF-β" as used throughout the specification will be understood to mean a protein with at least 50% sequence identity to human TGF-β1. A TGF-β protein may be identified, for example, by the BLAST algorithm.

The amino acid sequence of the human form of TGF-β1 is provided in Genbank Accession No. NP_000651. The nucleotide sequence of the mRNA is provided in GenBank Accession No. NM_000660.

The amino acid sequence of the human form of TGF-β1 is provided in Genbank Accession No. NP_003229. The nucleotide sequence of the mRNA is provided in GenBank Accession No. NM_003238.

The amino acid sequence of the human form of TGF-β3 is provided in Genbank Accession No. NP_003230. The nucleotide sequence of the mRNA is provided in GenBank Accession No. NM_003239.

In the case where wound repair is improved, the agent may decrease expression and/or activity of TGF-β1, and/or increase the expression and/or activity of TGF-β3.

In the case where wound repair is decreased, the agent may increase the expression and/or activity of TGF-β1.

The agent in the various embodiments of the present invention may also modulate the expression, activity and/or secretion of collagen in cells involved in repair of the wound. Collagen is a major component of skin, cartilage, bone, and other connective tissue. There are a number of types of collagen, including type I collagen, and type II collagen.

In particular, the agent may modulate the expression and/or secretion of collagen I.

The amino acid sequence of the human form of collagen, type I, alpha 1 is provided in Genbank Accession No. NP_000079. The nucleotide sequence of the mRNA is provided in GenBank Accession No. NM_000088.

In the case where wound repair is improved, the agent may decrease the expression, activity and/or secretion of collagen I.

In the case where, where wound repair is decreased, the agent may increase the expression, activity and/or secretion of collagen I.

The present invention may also be used to prepare a medicament for modulating wound repair.

Accordingly, in another embodiment the present invention provides the use of an agent that modulates expression and/or activity of Flightless I in the preparation of a medicament for modulating wound repair.

Examples of agents are as previously described herein.

For example, the agent may be used in the preparation of a medicament for improving wound repair. In this case, the agent may decrease the expression and/or activity of Flightless I. An example of such an agent is a neutralising antibody to Flightless I (or an antigen binding part thereof), such as an antibody to the leucine rich repeat domain of the protein.

The agent may be delivered to the wound by a suitable method known in the art. Methods of delivery include direct exposure of cells in the wound to the agent, such as by the use of a topical composition, intradermal injection of the agent to the wound and/or around the wound, and administration of the agent to a subject.

In the case of administration of an agent to a subject, the agent may be administered to the subject in a suitable form to effect modulation of the expression and/or activity of Flightless I in cells involved in repair of the wound.

The effective amount of agent to be delivered or administered is not particularly limited, so long as it is within such an amount and in such a form that generally exhibits a pharmacologically useful or therapeutic effect.

In this regard, an effective amount of the agent may be appropriately chosen, depending upon, for example, the type of wound, the mode of delivery, the age and body weight of the subject, the frequency of delivery or administration, and the presence of other active agents.

In one embodiment, the agent is delivered or administered as a pharmaceutical composition to modulate repair of a wound.

Accordingly, in another form the present invention provides a pharmaceutical composition when used to modulate repair of a wound, the composition including an effective amount of an agent that modulates expression and/or activity of Flightless I.

For example, a neutralising antibody to Flightless I may be formulated into a topical composition for topical administration to a wound, or the neutralising antibody may be formulated into a composition for injection into one or more regions near or surrounding the wound.

Accordingly, in another embodiment the present invention provides a topical wound healing composition, the composition including a therapeutically effective amount of an agent that reduces expression and/or activity of Flightless I in cells involved in wound repair.

In one embodiment, the topical wound healing composition is a composition including a therapeutically effective amount of a neutralising antibody to Flightless I. Topical compositions including an antibody are generally as described in U.S. Pat. No. 5,702,946.

The present invention may also be used to modulate scar formation.

Accordingly, in another embodiment the present invention provides a method of modulating scar formation in a wound of a subject, the method including the step of delivering to a wound in a subject an effective amount of an agent that modulates expression and/or activity of Flightless I.

In this regard, where the rate of wound healing is increased, there is often an associated increase in scar formation. Thus, modulating the expression and/or activity of Flightless I may be used to modulate scar formation.

Methods for assessing the extent of scar formation are known in the art.

Examples of suitable agents are as previously described herein.

As discussed previously, in one embodiment the agent may delivered to the wound by administration of the agent to the wound and/or a region(s) near the wound. For example, the agent may be formulated into a topical composition for administration to the wound, and/or the agent may be formulated into a composition for injection into a region(s) near and/or surrounding the wound.

In one embodiment, scar formation is reduced. In this case, the agent may increase the expression and/or activity of Flightless I in cells involved in repair of a wound.

The present invention may also used in the preparation of a medicament for modulating scar formation.

Accordingly, in another embodiment the present invention provides the use of an agent that modulates expression and/or activity of Flightless I in the preparation of a medicament for modulating scar formation.

In one embodiment, the medicament is used to reduce scar formation. In this case, the agent may increase the expression and/or activity of Flightless I in cells involved in repair of a wound.

In another embodiment, the agent may be prepared into a pharmaceutical composition to modulate scar formation.

Accordingly, in another embodiment the present invention provides a pharmaceutical composition when used to modulate scar formation, the composition including an effective amount of an agent that modulates expression and/or activity of Flightless I.

In one embodiment, the composition is a topical composition.

The present invention may also be used to prevent and/or treat a disease, condition or state associated with undesired or abnormal fibrosis in a subject.

Accordingly, in another embodiment the present invention provides a method of preventing and/or treating a disease, condition or state associated with undesired or abnormal fibrosis in a subject, the method including the step of administering to the subject a therapeutically effective amount of an agent that modulates expression and/or activity of Flightless I.

In this regard, it will be understood that the agent modulates expression and/or activity of Flightless I in cells involved with the fibrosis.

Examples of diseases, conditions and states associated with abnormal or undesired fibrosis include atherosclerosis; fibrotic diseases of the lung, liver, kidney and cardiovascular system; excessive wound healing; and cancer. Accordingly, the present invention may be used to prevent and/or treat such diseases, conditions or states.

In one embodiment, the agent increases the expression and/or activity of Flightless I. Examples of such agents are as previously described herein.

The present invention may also be used in the preparation of a medicament for preventing and/or treating a disease, condition or state associated with undesired or abnormal fibrosis.

Accordingly, in another embodiment the present invention provides the use of an agent that modulates expression and/or activity of Flightless I in the preparation of a medicament for preventing and/or treating a disease, condition or state associated with undesired or abnormal fibrosis.

The agent may also be prepared into a pharmaceutical composition used for preventing and/or treating a disease, condition or state associated with undesired or abnormal fibrosis.

Accordingly, in another embodiment the present invention provides a pharmaceutical composition when used to prevent and/or treat a disease, condition or state associated with undesired or abnormal fibrosis, the composition including an effective amount of an agent that modulates expression and/or activity of Flightless I.

The present invention may also be used to modulate one or more of expression, secretion and/or activity of TGF-β and/or collagen.

Accordingly, in another embodiment the present invention provides a method of modulating one or more of expression, secretion and/or activity of TGF-β and/or collagen, the method including the step of modulating expression and/or activity of Flightless I in a cell.

In one embodiment, the cell is a cell involved in wound repair and/or scar formation, such as a fibroblast or a keratinocyte.

In one embodiment, the cell is a human cell or an animal cell, such as a cell present in vivo in a human or animal.

For example, the cell may be a cell involved in repair of a wound in a subject, a cell involved in scar formation in a subject, or a cell involved with fibrosis in a subject.

In one embodiment, the method is used to reduce the extent or rate of fibrosis in the subject.

In one embodiment, the expression and/or activity of TGF-β1 is modulated

In this case, decreasing expression and/or activity of Flightless I in the cell results in a decrease in the expression and/or activity of TGF-β1 in the cell and/or an decrease in the expression and/or secretion of collagen in the cell. Under these conditions, repair of a wound in a subject is improved.

In another embodiment, increasing expression and/or activity of Flightless I in the cell results in an increase in expression and/or activity of TGF-β1 in the cell and/or an increase in the expression and/or secretion of collagen in the cell. Under these conditions, the extent of scarring of a wound, or the extent or rate of fibrosis, in a subject is reduced.

In another embodiment, the expression and/or activity of TGF-β3 is modulated.

In this case, decreasing expression and/or activity of Flightless I in the cell results in an increase in the expression and/or activity of TGF-β3 in the cell and/or an decrease in the expression and/or secretion of collagen in the cell. Under these conditions, repair of a wound in a subject is improved.

In one embodiment, the expression and/or secretion of collagen type I is modulated.

The present invention may also be used for the preparation of a medicament for modulating expression and/or activity of TGF-β and/or collagen.

Accordingly, in another embodiment the present invention provides the use of an agent that modulates the expression and/or activity of Flightless I in the preparation of a medicament for modulating expression and/or activity of TGF-β and/or collagen.

The present invention may also be used in a pharmaceutical composition used to modulate expression and/or activity of TGF-β and/or collagen.

Accordingly, in another embodiment the present invention provides a pharmaceutical composition when used to modulate expression and/or activity of TGF-β and/or collagen, the composition including an effective amount of an agent that modulates expression and/or activity of Flightless I.

The present invention may also be used to modulate migration and/or proliferation of a cell involved in wound repair, scar formation or fibrosis.

Accordingly, in another embodiment the present invention provides a method of modulating migration and/or proliferation of a cell involved in wound repair, scar formation or fibrosis, the method including the step of modulating the expression and/or activity of Flightless I in the cell.

Methods for assessing migration and proliferation of cells are known in the art.

In one embodiment, the cell is a fibroblast, a keratinocyte or an inflammatory cell.

In one embodiment, the cell is a human cell or an animal cell, such as a cell present in vivo in a human or animal.

For example, the cell may be a cell involved in repair of a wound in a subject, a cell involved in scar formation in a subject, or a cell involved with fibrosis in a subject.

In one embodiment, decreasing expression and/or activity of Flightless I increases migration and/or proliferation of a cell.

In another embodiment, increasing expression and/or activity of Flightless I decreases migration and/or proliferation of a cell.

In one embodiment, the modulation of expression and/or activity of Flightless I is achieved by delivering or exposing the cell to an agent that modulates the expression and/or activity of Flightless I. For example, the agent may be delivered to the cells by exposing the cells to the agent, or in the case of a subject, administering the agent to the subject.

Examples of suitable agents are as previously described herein.

In one embodiment the agent decreases the expression and/or activity of Flightless I in the cell. An example of such an agent is a neutralising antibody or an antigen binding portion thereof, such as a neutralising antibody to Flightless I. Examples of antibodies are previously described herein.

The present invention may also be used for the preparation of a medicament for modulating migration and/or proliferation of a cell involved in wound repair, scar formation or fibrosis.

Accordingly, in another embodiment the present invention provides the use of an agent that modulates the expression and/or activity of Flightless I in the preparation of a medicament for modulating migration and/or proliferation of a cell involved in wound repair, scar formation or fibrosis.

The present invention may also be used for the preparation of a pharmaceutical composition to modulate migration and/or or proliferation of a cell involved in wound repair, scar formation or fibrosis.

Accordingly, in another embodiment the present invention provides a pharmaceutical composition when used to modulate migration and/or proliferation of a cell involved in wound repair, scar formation or fibrosis, the composition including an effective amount of an agent that modulates expression and/or activity of Flightless I.

The delivery or administration of the agent in the various embodiments of the present invention may be within any time suitable to produce the desired effect of directly or indirectly modulating the expression and/or activity of Flightless I.

In this regard, in the case of modulating wound repair or scar formation, the modulation of expression and/or activity of Flightless I in the cell may occur at any one or more of the time of wounding, during healing of the wound and prior to wounding.

In the case of modulating fibrosis, the modulation of expression and/or activity of Flightless I in the cell may occur at either or both of prior to fibrosis occurring, and during fibrosis.

The agent in the various embodiments of the present invention may be delivered, exposed or administered by a suitable method.

In the case of the agent being administered to a subject, the agent may be administered orally, parenterally, topically, by injection, systemically or by any other suitable means, and therefore transit time of the agent must be taken into account.

In the case of a wound, the agent may for example be administered directly to the wound and/or a region(s) near and/or surrounding the wound.

In the case of fibrosis, the agent may be delivered to the site of fibrosis directly and/or administered to a subject so as to reach the site of fibrosis. For example, the agent may be administered systemically.

The delivery or administration of the agent in the various embodiments of the present invention may be delivery or administration of the agent alone, or delivery or administration of the agent formulated into a suitable pharmaceutical composition.

In this regard, the pharmaceutical composition may also include the use of one or more pharmaceutically acceptable additives, including pharmaceutically acceptable salts, amino acids, polypeptides, polymers, solvents, buffers, excipients and bulking agents, taking into consideration the particular physical and chemical characteristics of the agent to be administered.

The preparation of such pharmaceutical compositions is known in the art, for example as described in Remington's Pharmaceutical Sciences, 18th ed., 1990, Mack Publishing Co., Easton, Pa. and U.S. Pharmacopeia: National Formulary, 1984, Mack Publishing Company, Easton, Pa.

For example, the agent can be prepared into a variety of pharmaceutical compositions in the form of, e.g., an aqueous solution, an oily preparation, a fatty emulsion, an emulsion, a gel, etc., and these preparations can be administered as intramuscular or subcutaneous injection or as injection to an organ, or as an embedded preparation or as a transmucosal preparation through nasal cavity, rectum, uterus, vagina, lung, etc. The composition may be administered in the form of oral preparations (for example solid preparations such as tablets, capsules, granules or powders; liquid preparations such as syrup, emulsions or suspensions). Compositions containing the agent may also contain a preservative, stabiliser, dispersing agent, pH controller or isotonic agent. Examples of suitable preservatives are glycerin, propylene glycol, phenol or benzyl alcohol. Examples of suitable stabilisers are dextran, gelatin, a-tocopherol acetate or alpha-thioglycerin. Examples of suitable dispersing agents include polyoxyethylene (20), sorbitan mono-oleate (Tween 80), sorbitan sesquioleate (Span 30), polyoxyethylene (160) polyoxypropylene (30) glycol (Pluronic F68) or polyoxyethylene hydrogenated castor oil 60. Examples of suitable pH controllers include hydrochloric acid, sodium hydroxide and the like. Examples of suitable isotonic agents are glucose, D-sorbitol or D-mannitol.

The administration of the agent in the various embodiments of the present invention may also be in the form of a composition containing a pharmaceutically acceptable carrier, diluent, excipient, suspending agent, lubricating agent, adjuvant, vehicle, delivery system, emulsifier, disintegrant, absorbent, preservative, surfactant, colorant, flavorant or sweetener, taking into account the physical and chemical properties of the agent being administered.

For these purposes, the composition may be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

The carrier may contain minor amounts of additives, such as substances that enhance solubility, isotonicity, and chemical stability, for example anti-oxidants, buffers and preservatives.

When administered orally, the agent will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

A tablet may be made by compressing or moulding the agent optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Moulded tablets may be made by moulding in a suitable machine, a mixture of the powdered active ingredient and a suitable carrier moistened with an inert liquid diluent.

The administration of the agent in the various embodiments of the present invention may also utilize controlled release technology. The agent may also be administered as a sustained-release pharmaceutical. To further increase the sustained release effect, the agent may be formulated with additional components such as vegetable oil (for example soybean oil, sesame oil, camellia oil, castor oil, peanut oil, rape seed oil); middle fatty acid triglycerides; fatty acid esters such as ethyl oleate; polysiloxane derivatives; alternatively, water-soluble high molecular weight compounds such as hyaluronic acid or salts thereof (weight average molecular weight: ca. 80,000 to 2,000,000), carboxymethylcellulose sodium (weight average molecular weight: ca. 20,000 to 400,000), hydroxypropylcellulose (viscosity in 2% aqueous solution: 3 to 4,000 cps), atherocollagen (weight average molecular weight: ca. 300,000), polyethylene glycol (weight average molecular weight: ca. 400 to 20,000), polyethylene oxide (weight average molecular weight: ca. 100,000 to 9,000,000), hydroxypropylmethylcellulose (viscosity in 1% aqueous solution: 4 to 100,000 cSt), methylcellulose (viscosity in 2% aqueous solution: 15 to 8,000 cSt), polyvinyl alcohol (viscosity: 2 to 100 cSt), polyvinylpyrrolidone (weight average molecular weight: 25,000 to 1,200,000).

Alternatively, the agent may be incorporated into a hydrophobic polymer matrix for controlled release over a period of days. The agent may then be moulded into a solid implant, or externally applied patch, suitable for providing efficacious concentrations of the agent over a prolonged period of time without the need for frequent re-dosing. Such controlled release films are well known to the art. Other examples of polymers commonly employed for this purpose that may be used include nondegradable ethylene-vinyl acetate copolymer a degradable lactic acid-glycolic acid copolymers which may be used externally or internally. Certain hydrogels such as poly(hydroxyethylmethacrylate) or poly(vinylalcohol)

also may be useful, but for shorter release cycles than the other polymer release systems, such as those mentioned above.

The carrier may also be a solid biodegradable polymer or mixture of biodegradable polymers with appropriate time release characteristics and release kinetics. The agent may then be moulded into a solid implant suitable for providing efficacious concentrations of the agent over a prolonged period of time without the need for frequent re-dosing. The agent can be incorporated into the biodegradable polymer or polymer mixture in any suitable manner known to one of ordinary skill in the art and may form a homogeneous matrix with the biodegradable polymer, or may be encapsulated in some way within the polymer, or may be moulded into a solid implant.

For topical administration, the composition of the present invention may be in the form of a solution, spray, lotion, cream (for example a non-ionic cream), gel, paste or ointment. Alternatively, the composition may be delivered via a liposome, nanosome, or nutri-diffuser vehicle.

A cream is a formulation that contains water and oil and is stabilized with an emulsifier. Lipophilic creams are called water-in-oil emulsions, and hydrophilic creams oil-in-water emulsions. The cream base for water-in-oil emulsions are normally absorption bases such as vaseline, ceresin or lanolin. The bases for oil-in-water emulsions are mono-, di- and triglycerides of fatty acids or fatty alcohols with soaps, alkyl sulphates or alkyl polyglycol ethers as emulsifiers.

A lotion is an opaque, thin, non-greasy emulsion liquid dosage form for external application to the skin, which generally contains a water-based vehicle with greater than 50% of volatiles and sufficiently low viscosity that it may be delivered by pouring. Lotions are usually hydrophilic, and contain greater than 50% of volatiles as measured by LOD (loss on drying). A lotion tends to evaporate rapidly with a cooling sensation when rubbed onto the skin.

A paste is an opaque or translucent, viscous, greasy emulsion or suspension semisolid dosage form for external application to the skin, which generally contains greater than 50% of hydrocarbon-based or a polyethylene glycol-based vehicle and less than 20% of volatiles. A paste contains a large proportion (20-50%) of dispersed solids in a fatty or aqueous vehicle. An ointment tends not to evaporate or be absorbed when rubbed onto the skin.

An ointment is an opaque or translucent, viscous, greasy emulsion or suspension semisolid dosage form for external application to the skin, which generally contains greater than 50% of hydrocarbon-based or a polyethylene glycol-based vehicle and less than 20% of volatiles. An ointment is usually lipophilic, and contains >50% of hydrocarbons or polyethylene glycols as the vehicle and <20% of volatiles as measured by LOD. An ointment tends not to evaporate or be absorbed when rubbed onto the skin.

A gel is usually a translucent, non-greasy emulsion or suspension semisolid dosage form for external application to the skin, which contains a gelling agent in quantities sufficient to impart a three-dimensional, cross-linked matrix. A gel is usually hydrophilic, and contains sufficient quantities of a gelling agent such as starch, cellulose derivatives, carbomers, magnesium-aluminum silicates, xanthan gum, colloidal silica, aluminium or zinc soaps.

The composition for topical administration may further include drying agents, anti-foaming agents; buffers, neutralizing agents, agents to adjust pH; colouring agents and decolouring agents; emollients; emulsifying agents, emulsion stabilizers and viscosity builders; humectants; odorants; preservatives, antioxidants, and chemical stabilizers; solvents; and thickening, stiffening, and suspending agents, and a balance of water or solvent.

It should also be appreciated that other methods of delivery of an agent to modulate the expression and/or activity of Flightless I are contemplated. For example, the agent may be delivered by way of a nucleic acid or vector that allows for expression of the agent in the appropriate target cells. For example, the agent may be delivered by way of a viral vector that causes expression of the agent in target cells.

In this regard, the present invention specifically contemplates gene therapy methods, and in particular, gene therapy methods for correcting defects in diseases, conditions and states as previously described herein. Methods for gene therapy are known in the art.

Viral and gene therapy techniques are as generally described in "Viral Vectors for Gene Therapy: Methods and Protocols" Edited by Jules G Constant, Curtis A Machida (2003) Humana Press Inc., "Gene Delivery to Mammalian Cells: Viral Gene Transfer Techniques" Edited by William C Heiser (2004) Humana Press Inc., "Viruses in Human Gene Therapy" Edited by J. H. Vos (1995) Carolina Academic Press, and "Viral Therapy Of Human Cancers" Edited by J. G. Sinkovics and J. C. Horwath (2005) Marcel Dekker.

As described previously herein, the cell in the various relevant forms of the present invention may be a cell in vitro, or a cell in a biological system.

In this regard, the present invention also provides an isolated skin cell, or a progenitor or derivative thereof, in which the expression and/or activity of Flightless I in the skin cell is altered.

Accordingly, in another embodiment the present invention provides an isolated skin cell, or a progenitor or derivative thereof, the cell having an altered expression and/or activity of Flightless I.

Isolated skin cells, in which the expression and/or activity of Flightless I in the skin cell is altered, may have use as therapeutic or cosmetic agents. In one embodiment, the cell is a fibroblast cell or a keratinocyte cell.

Methods for altering the expression and/or activity of Flightless I in the cell are as previously herein described.

For example, to alter the expression and/or activity of Flightless I, an exogenous form of the protein or a regulator of the protein may be cloned and introduced into a cell by a suitable method known in the art. For example, a nucleic acid may be isolated and cloned into a suitable expression vector for use in the cell type of interest by methods known in the art. Methods for the isolation of nucleic acid sequences and their cloning into a suitable expression vector are essentially as described in Sambrook, J, Fritsch, E. F. and Maniatis, T. Molecular Cloning: A Laboratory Manual 2nd. ed. Cold Spring Harbor Laboratory Press, New York. (1989). The recombinant molecule may then be introduced into the cell and the cloned nucleic acid expressed.

In the case where an exogenous nucleic acid is introduced into cells by way of being cloned into (or expressed from) a vector, suitable vectors include plasmid vectors and viral vectors.

The vector may also further include regulatory elements for the expression of inserted nucleic acids, for example inducible or consititutive promoters for driving the expression of an inserted nucleic acid in a particular cell type, poly A signals for efficient polyadenylation of mRNA transcribed from inserted nucleic acids, or other regulatory elements to control translation, transcription or mRNA stability, all known in the art.

In the case of introducing an exogenous nucleic acid into a cell to express a target gene, the expression may be achieved by a number of methods known in the art. These include transient or stable transfection of cells with a recombinant nucleic acid encoding the gene of interest under the control of a promoter that is active in the particular cell type.

In the case of introducing an exogenous nucleic acid into a cell to decrease the expression of a target gene, a decrease in expression may be achieved by a number of methods known in the art. These include the use of an antisense nucleic acid that binds to an endogenous mRNA and which interferes with translation, the use of a molecule that can specifically repress transcription of the endogenous mRNA such as a specific DNA or RNA binding protein, a nucleic acid capable of forming a triple helix structure, a small interfering RNA (siRNA), a microRNA, or a ribozyme that can cleave a specific mRNA.

Generally, the introduction of exogenous nucleic acids to decrease the expression of a target gene will involve constitutive expression in the cell of the nucleic acid. However, under some circumstances it may be appropriate to express the nucleic acid by use of an inducible promoter.

Methods for introducing nucleic acids into cells, and expressing proteins, are known in the art. For example, a nucleic acid may be introduced into a cell by various methods, including transformation using calcium phosphate, viral infection, electroporation, lipofection, and particle bombardment. Methods for introducing DNAs into cells are essentially as described in Sambrook, J, Fritsch, E. F. and Maniatis, T. Molecular Cloning: A Laboratory Manual 2nd. ed. Cold Spring Harbor Laboratory Press, New York. (1989).

As described previously herein, the expression and/or activity of Flightless I in the cell may be altered for example by the introduction of an exogenous nucleic acid into the cell. Alternatively, the expression and/or activity of Flightless I may be altered by a manipulation of an endogenous nucleic acid in the cell, such as by alteration of the Flightless I gene itself or a regulator of Flightless I expression.

Accordingly, in another form the present invention also provides an isolated skin cell, or a progenitor or derivative thereof, wherein the cell includes a nucleic acid that modulates Flightless I expression and/or activity in the cell.

Methods for introducing nucleic acids into cells are known in the art and are as previously described herein.

In one embodiment, the altered expression and/or activity of Flightless I is due to introduction of an exogenous nucleic acid into the cell. In another embodiment the altered expression and/or activity of Flightless I is due to an alteration of an endogenous nucleic acid in the cell.

In one embodiment, the nucleic acid is integrated into the genome, such as a suitable transgene. However, it will be appreciated that the cell may also be, for example, a transiently transfected cell.

In one embodiment, the isolated cell in the various forms of the present invention also has an altered expression and/or activity of TGF-β and/or an altered expression and/or secretion of collagen.

The cells of the present invention may also be part of a whole animal. Accordingly, in another form the present invention provides an animal including one or more skin cells in which the expression and/or activity of Flightless I is altered.

In another form, the present invention provides an animal with one or more skin cells including a nucleic acid that modulates Flightless I expression and/or activity in the cell.

Examples of such animals are chimeric animals or transgenic animals. Methods for producing such animals are known in the art.

The cells of the present invention may have use in, for example, wound repair, reducing scar formation and in preventing and/or treating a disease, condition or state in a subject associated with undesired or abnormal fibrosis. For example, the cells may be delivered to a desired site of action to provide a therapeutic or beneficial effect. In this regard, the cells may be delivered to the site in an appropriate composition to exert their therapeutic or beneficial effect. Compositions for maintaining and delivering cells are known in the art.

The present invention also provides methods for screening new agents that may modulate one or more of wound repair, scar formation and migration and/or proliferation of cells involved in wound repair.

Accordingly, in another embodiment the present invention provides a method of identifying an agent that modulates wound repair, the method including identifying an agent that modulates one or more of expression, secretion and activity of Flightless I.

In one embodiment, the identification of the agent includes identifying an agent that modulates one or more of expression, secretion and activity of Flightless I in cells involved in wound repair. Examples of cells involved in wound repair are as previously discussed herein.

In one embodiment, the screening method may be used to identify an agent that promotes wound repair. For example, the agent may decrease Flightless I activity.

In another embodiment, the screening method may be use to identify an agent that reduces scar formation. For example, the agent may increase Flightless I activity.

In another embodiment, the screening method may be used to identify an agent that modulates migration and/or proliferation of cells involved in wound repair.

The present invention also provides an agent identified by the screening methods, and the use of the agents to modulate for example wound repair, scar formation and fibrosis.

Finally, standard techniques may be used for recombinant DNA technology, oligonucleotide synthesis, and tissue culture and transfection (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989) and Ausubel, F. M. et al. (1989) Current Protocols in Molecular Biology, John Wiley & Sons, New York, N.Y.

DESCRIPTION OF SPECIFIC EMBODIMENTS

Reference will now be made to experiments that embody the above general principles of the present invention. However, it is to be understood that the following description is not to limit the generality of the above description.

EXAMPLE 1

Antibodies

Mouse monoclonal anti-FliI antibody (sc-21716) and rabbit anti-TGF-β1 polyclonal antibody (se-146) were obtained from Santa Cruz Biotechnology (CA, USA) whilst goat anti TGF-βs3 was obtained from R&D Systems (MN, USA). Rabbit polyclonal anti-Collagen I was obtained from Monosan (Uden, The Netherlands). FITC-conjugated phalloidin was purchased from Sigma-Aldrich (Sydney, Australia). Affinity purified rabbit anti-FliL antibodies raised against the leucine rich repeat domain of the FliI protein has been previously described (Davy, D. A. et al. 2001. The flightless I protein colocalizes with actin- and microtubule-based structures in motile Swiss 3T3 fibroblasts: evidence for the involvement of PI 3-kinase and Ras-related small GTPases. *J Cell Sci* 114:549-562).

EXAMPLE 2

FliI Deficient+/− and Transgenic Mice

All studies were performed in mice with the BALB/c background. FliI deficient heterozygous null mice (FliI+/−) and mice carrying the complete human FliI gene on a cosmid transgene were as described previously (Campbell, H. D. et al. 2002. Fliih, a gelsolin-related cytoskeletal regulator essential for early mammalian embryonic development. *Mol Cell Biol* 22:3518-3526).

Heterozygous transgenic mice (Tg1) were made by crossing FliI+/+ with cosmid transgene+/−. These transgenic mice were intercrossed to obtain animals homozygous for the transgene (Tg2; FliI+/+, cosmid transgene+/+). An independent transgenic line (Tg3) was made by excising the FliI gene from cosmid c110H8 (Campbell, H. D. et al. 2002. Fliih, a gelsolin-related cytoskeletal regulator essential for early mammalian embryonic development. *Mol Cell Biol* 22:3518-3526) as a 17.8 kb BspHI fragment. This fragment contains ~4 kb of 5'-flanking sequence extending into the 5' end of the next identified gene, and at the 3' end contains a small portion of the overlapping 3' end of the LLGL gene. The fragment was cloned into the NcoI site of LITMUS-29 (New England Biolabs, Ipswich, USA) and was resected as an SpeI-NsiI fragment for preparation of transgenic mice, (FliI+/+, 17.8 kb transgene+/−) using BALB/c ES cells as described previously (Campbell, H. D. et al. 2002. Fliih, a gelsolin-related cytoskeletal regulator essential for early mammalian embryonic development. *Mol Cell Biol* 22:3518-3526). ES cells were cotransfected with pMC1NeoPolyA to allow co-selection with G418. ES cells were screened, chimaera were prepared and bred and transgenic mice were genotyped as described previously (Campbell, H. D. et al. 2002. Fliih, a gelsolin-related cytoskeletal regulator essential for early mammalian embryonic development. *Mol Cell Biol* 22:3518-3526).

EXAMPLE 3

Murine Surgical Techniques

FliI transgenic mice (Tg1-3; female 16-20 weeks old) and wild-type sex and age-matched litter mates were wounded using the same protocol previously described in (Cowin, A. J. et al. 2006. Wound Healing Is Defective in Mice Lacking Tetraspanin CD151. *J Invest Dermatol*.). Briefly, two equidistant 1 cm full thickness incisions were made through the skin and left to heal by secondary intention. Digital photographs were taken of the wounds at 0, 3, 7, 14 and 21 days post-wounding. A ruler was aligned next to the wound to allow direct wound area and wound gape (mid-point of the 1 cm incision) measurements to be made. Wounds were harvested at 3, 7, 14 and 21 days and were bisected. One half was fixed in 10% buffered formalin and processed so that the midpoint of the wound was sectioned and compared between groups. The other half was microdissected to remove any contaminating normal, unwounded skin and snap frozen in liquid nitrogen for RNA and protein extraction. FliI deficient+/− mice (female 16-20 weeks old) and sex and age-matched wild-type littermates were wounded similarly to reported studies (Cowin, A. J. et al. 2001. Hepatocyte growth factor and macrophage-stimulating protein are upregulated during excisional wound repair in rats. *Cell Tissue Res* 306: 239-250). Briefly, two standardised 1 $cm^2$ full thickness excisions were made using fine scissors on the flanks of the animals extending 3.5-4.5 cm from the base of the skull, 1 cm either side of the spinal column. Wounds were harvested and processed as described above. To a subset of wild type sex and age-matched mice, a single intradermal injection of 100 µl of either FliL or rabbit IgG was injected into the wound margins of incisional wounds created as described above and left for 7 days prior to wound harvesting and processing.

EXAMPLE 4

Histology, Immunohistochemistry and Image Analysis

Histological sections (4 µm) were cut from paraffin-embedded fixed tissue. Sections were stained with hematoxylin and eosin or subjected to immunohistochemistry following antigen retrieval according to the manufacturer's protocols (DAKO Corporation, Botany, Australia). Following blocking in 3% normal horse serum, primary antibodies against FliI (1:400), TGF-β1 (1:200), collagen I (1:200) or gelsolin (1:100) were applied. Species-specific, biotinylated secondary antibodies (1:200) were used and detection was by CY3-conjugated streptavidin (1:200) (Sigma-Aldrich, Sydney, Australia). Integrated fluorescence intensity was determined using AnalySIS software package (Soft Imaging System GmbH, Munster Germany). Cell proliferation was determined using the proliferating cell nuclear antigen (PCNA) immunostaining technique (Geier, M. S. et al. 2005. Development and resolution of experimental colitis in mice with targeted deletion of dipeptidyl peptidase IV. *J Cell Physiol* 204:687-692). The number of PCNA positive cells were counted and expressed as a percentage of total cells within the wound. Negative controls included replacing primary antibodies with normal rabbit IgG, normal mouse or normal goat IgG. Non-specific binding was determined by omitting primary or secondary antibodies. All control sections had negligible immunofluorescence.

EXAMPLE 5

Histological Image Analysis

Image analysis was performed using the ImageProPlus program (MediaCybernetics Inc., Maryland, USA). Wound size was determined by manually drawing below the epidermis or clot between the wound margins. The percentage of the wound that had reepithelialised was determined by measuring the portions of the wound that were covered with epidermis as a percentage of the entire wound. Dermal gape was determined by measuring between the dermal wound margins. Blinded measurements of histological slides by two independent assessors was performed.

EXAMPLE 6

In Vitro Assays

Primary human foreskin fibroblasts (HFFs) and keratinocytes (HaCaTs) were used in the in vitro assays. Primary fibroblasts were also cultured from wild-type and FliI over-expressing (Tg1) mouse skins. Briefly, punch biopsies taken from wild-type and Tg1 mice skin were washed with PBS, allowed to adhere to the base of culture dishes and then cultured in DMEM supplemented with 10% FBS, penicillin and streptomycin (50 U ml$^{-1}$) for several days. After removal of biopsy, adherent cells were trypsinized and maintained in culture.

EXAMPLE 7

Cell Proliferation Assay

HFFs and HaCaTs were cultured until confluent in a 37° C., 5% $CO_2$ incubator before seeding into 96-well plates at a density of $4\times10^4$ cells/well. After 24 hours the media was replaced with serum-free DMEM and incubated for 4 hours to synchronise cell cycle. Cell proliferation assays were performed using the metabolic substrate WST-1 according to manufacturer's protocols (Roche Applied Science, Munich, Germany). Briefly, 10 μl of WST-1 reagent was added to the cells and left at 37° C. for 30 minutes. The presence of the formazan product is quantified using a dual absorbance of 450 nm and 600 nm using a plate reader.

EXAMPLE 8

Scratch Wound Assay

HFFs and HaCaTs were grown to confluence in DMEM with 10% FBS in 6-well plates then scratched with a P200 pipette tip, producing a wound of approximately 2 mm×1 cm. The cells were photographed at 0, 3, 6, 12, 24, 27, 30 and 48 hours. Wound margins were measured using the Image Pro-Plus program (MediaCybernetics Inc., Silver Springs, Md., USA) and rate of closure quantified as percent of initial wound area.

EXAMPLE 9

Immunocytochemistry

HFFs and HaCaTs were grown to confluence on glass cover slips in DMEM containing 10% FBS. Cells were fixed with acetone for 5 minutes and blocked with 1% BSA/PBS for 15 minutes. FliI (1:400; 1 hour incubation at room temperature) and phalloidin-FITC (1:250 of 100 μg/ml; 30 minutes incubation at room temperature) were added to the cells. Biotinylated anti-mouse (1:200, Sigma-Aldrich, Sydney, Australia) was added for 1 hour and detected by CY3-conjugated streptavidin (1:200). Integrated fluorescence intensity was determined as before.

EXAMPLE 10 siRNA Knockdown of FliI

HFFs and HaCaTs were seeded into 6-well plates and cultured until 30-50% confluent at time of transfection. FliI siRNA (Lee, Y. H. et al. 2004. Developmentally essential protein flightless I is a nuclear receptor coactivator with actin binding activity. *Mol Cell Biol* 24:2103-2117) was transfected into the cells using Lipofectamine 2000 (Invitrogen, Carlsbad, Calif., USA). 250 μl FliI siRNA (optimised to final concentrations of 100 nM for HFFs, 60 nM for HaCaTs) in Opti-MEM I Reduced Serum Medium (Invitrogen, Carlsbad, Calif., USA) was incubated for 20 minutes at room temperature with 250 μl Lipofectamine 2000 to form an siRNA: Lipofectamine Complex. 500 μl siRNA:Lipofectamine 2000 complex was added to each well, mixed and cells incubated for 6 hours prior to replacing transfection media with 10% FBS growth medium. Cells were incubated for 24 to 48 hours for gene knockdown assessment.

EXAMPLE 11

Real-Time PCR

Total RNA was extracted from HFFs and HaCaTs using TRIzol reagent (Invitrogen, Carlsbad, Calif., USA) and RNeasy spin columns (Qiagen, Hilder, Germany) according to manufacturers' protocols. Contaminating genomic DNA was removed using a DNA-free-kit (Ambion, Austin, Tex., USA). cDNA was synthesized from 1 μg RNA using reverse transcriptase. cDNA together with specific primers were set up to a final concentration of 1×SYBR Green, 1× Amplitaq PCR Buffer, 3 mM $MgCl_2$, dNTPs (200 μM each), 0.9 μM of Primers (forward and reverse), 1.25 Units AmpliTaq Gold DNA polymerase in 25 μl $H_2O$. The primer sequences were as follows:

```
FliI forward,
                                    (SEQ ID NO: 1)
5'-CCTCCTACAGCTAGCAGGTTATCAAC-3';

reverse,
                                    (SEQ ID NO: 2)
5'-GCATGTGCTGGATATATACCTGGCAG-3'.

Cyclophilin A forward,
                                    (SEQ ID NO. 3)
5'-GGTTGGATGGCAAGCATGTG-3';

reverse,
                                    (SEQ ID NO: 4)
5'-TGCTGGTCTTGCCATTCCTG-3'.
```

EXAMPLE 12

Western Blotting

10 μg of protein extracted from skin fibroblasts was run on 12.5% SDS-PAGE gels and transferred to nitrocellulose by semi-dry transfer. Membranes were blocked in 15% skimmed milk powder for 10 minutes and FliI antibody (1:500) added in PBS/3% SMP/0.3% Tween20 for 1 hour. After two washes in PBS/3% SMP/0.3% Tween20 anti-mouse HRP-conjugated antibody (1:1000) was added for a further 1 hour. Stringent washes were performed before detection of HRP by ECL (Amersham Biosciences UK Limited, Buckinghamshire, UK) and exposure to X-ray film.

Skin fibroblasts were grown to confluence in DMEM (10% FBS), scratch wounded and incubated for a further 24 hours. The conditioned media was removed, concentrated using Centricon®Centrifugal Filter Columns (Millipore Australia Pty Ltd, North Ryde NSW) and protein concentration determined using Pierce BCA protein assay (Quantum Scientific, Paddington, Qld). The cells were lysed in lysis buffer (50 mM Tris pH 7.5, 1 mM EDTA, 50 mM NaCl, 0.5% Triton-X-100), containing Complete™ Mini protease inhibitor cocktail tablet (Roche Diagnostics Australia Pty. Ltd. Castle Hill NSW)/10 mls). and protein levels determined as before. Equal amounts of protein were loaded onto 12.5% SDS-PAGE gels and subjected to Western blotting for FliI as described above.

EXAMPLE 13

Statistical Analysis

Statistical differences were determined using the Student's t-test or an ANOVA. For data not following a normal distribution, the Mann-Whitney U test was performed. A P value of less than 0.05 was considered significant.

EXAMPLE 14

Scratch-Wounding Increases FliI Expression in Fibroblasts and Keratinocytes

To determine the effect of wounding on FliI expression in human skin cells in vitro, skin fibroblasts and keratinocytes were cultured to confluence, scratch-wounded and subsequently immunostained for FliI and F-actin over a 24 hour time-course. FliI protein was observed throughout the fibroblasts with both nuclear and cytoplasmic staining observed in unwounded fibroblasts (FIG. 1a,b). Wounding the fibroblast monolayer caused a significant increase in nuclear FliI staining (FIG. 1c,d) which peaked at 6 hours post-wounding (P=0.010 vs unwounded control) but returned to unwounded levels by 24 hours (FIG. 1i). When confluent keratinocytes were wounded the intensity of staining for FliI significantly increased 10 hours post-wounding (P=0.025 vs unwounded control) but FliI remained in the cytoplasm (FIG. 1 e-h, j).

Figure 2:
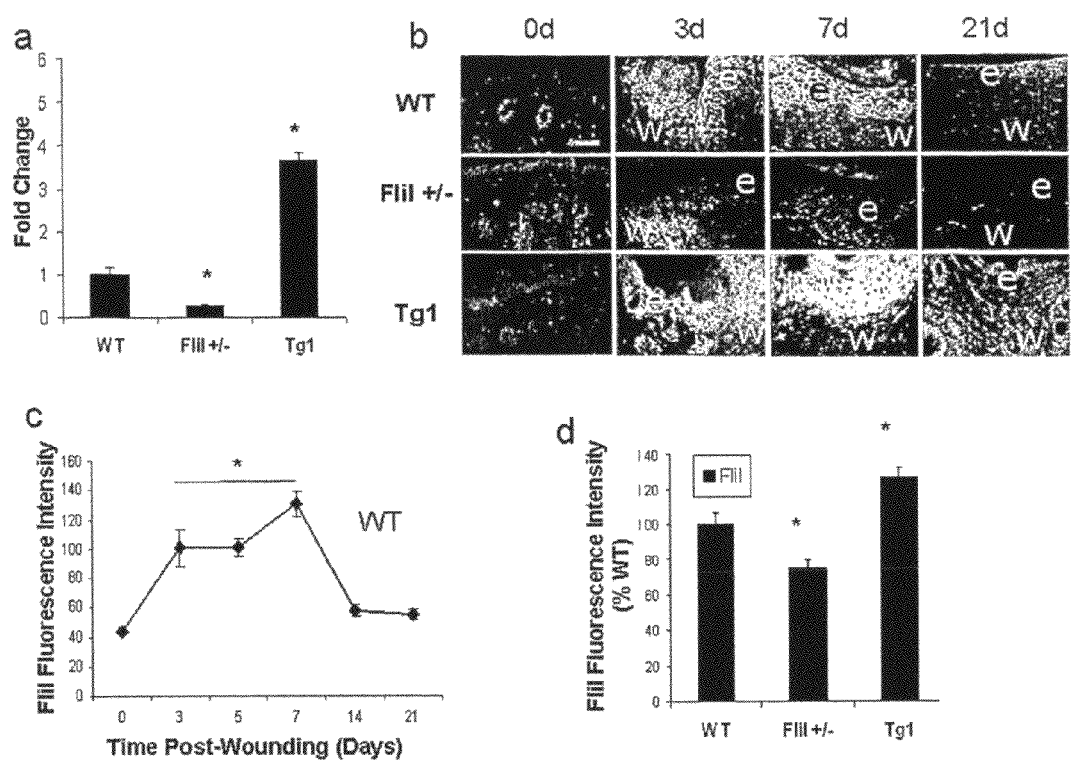
FIG. 2 shows that FliI is upregulated in response to wounding. (a) mRNA was extracted from the skin of wild-type, FliI deficient (+/−) and FliI transgenic (Tg1) mice and the expression of FliI was determined using Real-Time qPCR (n=3 for each group P=0.007 0 day+/− vs. 0 day WT; P=0.001 0 day Tg1 vs 0 day WT). (b) Immunohistochemistry for FliI protein was performed on wounded and unwounded wild-type (WT), FliI deficient+/− (+/−) and FliI transgenic (Tg1) mice skin. Representative images are shown for 0, 3, 7, and 21 day wounds. In all images, e denotes position of epidermis, w indicates position of wound. (c) In WT wounds, integrated fluorescence intensity quantitation of FliI expression in the skin shows FliI is significantly increased at 3 (P=0.002), 5 (P=0.0003) and 7 (P=0.015) days post-wounding, but by 21 days has returned to basal expression levels (n=6 per group). (d) Quantification of FliI protein expression in WT, +/−, and Tg1 wounds at 7 days post wounding. *denotes significance and P=0.007 7 day+/− vs. 7 day WT; P=0.011 7 day Tg1 vs 7 day WT). Results represent mean+/−s.e.m. (n=6). Scale bar in (b) refers to all and =50 µm.

The effect of FliI deficiency on wound healing was determined using mice heterozygous for the FliI gene knockout (FliI+/−) since homozygous deletion of FliI is embryonic lethal. The heterozygous null mice produce half the wild-type level of FliI (Campbell, H. D. et al. 2002. Fliih, a gelsolin-related cytoskeletal regulator essential for early mammalian embryonic development. *Mol Cell Biol* 22:3518-3526). Age-matched wild-type littermates were used in all experiments as controls. To determine the effect of overexpression of FliI on wound healing, we made FliI transgenic mice carrying extra copies of the human FliI gene. These mice showed no visible differences compared with control littermates and reached the same average lifespan. The fur appeared normal and histological analysis of the skins from all three transgenic mouse lines revealed no differences in skin architecture. To confirm the different levels of FliI in these mouse lines we extracted mRNA from unwounded skins and performed real-time qRT-PCR (FIG. 2a). Significantly reduced levels of FliI were observed in the FliI+/− skin whilst there was almost a 4 fold increase in FliI expression in the FliI Tg1 mouse skin (FIG. 2a).

EXAMPLE 15

FliI is Upregulated During Wound Healing In Vivo

Wounded and unwounded skin from wild-type, FliI deficient+/− and FliI transgenic mice (Tg1) was examined for FliI protein using immunohistochemistry. In wild-type mouse skin wounds, FliI was observed predominantly in the cytoplasm of basal epidermal keratinocytes, fibroblasts and the outer root sheath keratinocytes of hair follicles (FIG. 2b). Wounding significantly increased FliI levels in both keratinocytes within the migrating epidermis at the wound edge and in fibroblasts within the wound bed (FIG. 2b). Additionally, extracellular staining of FliI was observed within the wound matrix which was most obvious at 7 days post-wounding (FIG. 2b) A temporal effect of wounding on FliI localisation was observed with FliI staining peaking at 7 days post-injury (P=0.0015 vs unwounded skin, FIG. 2b,c) returning to basal levels by 14 days post-wounding (FIG. 2b,c).

In FliI deficient+/− wounds, there was significantly less staining for FliI in the skin of unwounded FliI+/− mice (P=0.007, P=0.001 vs wild-type 0 day wounds respectively; FIG. 2b). Even in the FliI+/− wounds, FliI did increase with wounding, peaking at 7 days post injury, but this increase was significantly less than that seen in equivalent wild-type wounds containing two functional copies of the gene (FIG. 2b,d). In contrast, wounds in the FliI transgenic mice showed markedly increased FliI expression compared to wild-type, particularly within the keratinocytes and fibroblasts at the wound edge, peaking at 7 days post-wounding (FIG. 2b,d).

EXAMPLE 16

FliI Overexpression Decreases Cell Proliferation, Reduces Migration and Impairs Wound Healing To identify the effect of FliI on skin cell function, the effect of increased FliI expression on fibroblast proliferation and migration was determined using primary fibroblasts derived from FliI transgenic (Tg1) mice. Significantly reduced proliferation was observed compared to their wild-type counterparts (P=0.017 FIG. 3a). Scratch wounds made in confluent monolayers of wild-type and FliI overexpressing fibroblasts closed significantly slower in the FliI overexpressing cultures indicating reduced migratory capacity (FIG. 3b, P<0.05 vs time-matched wild-type controls) although by 24 hours both sets of scratch wounds were closed.

Figure 3:
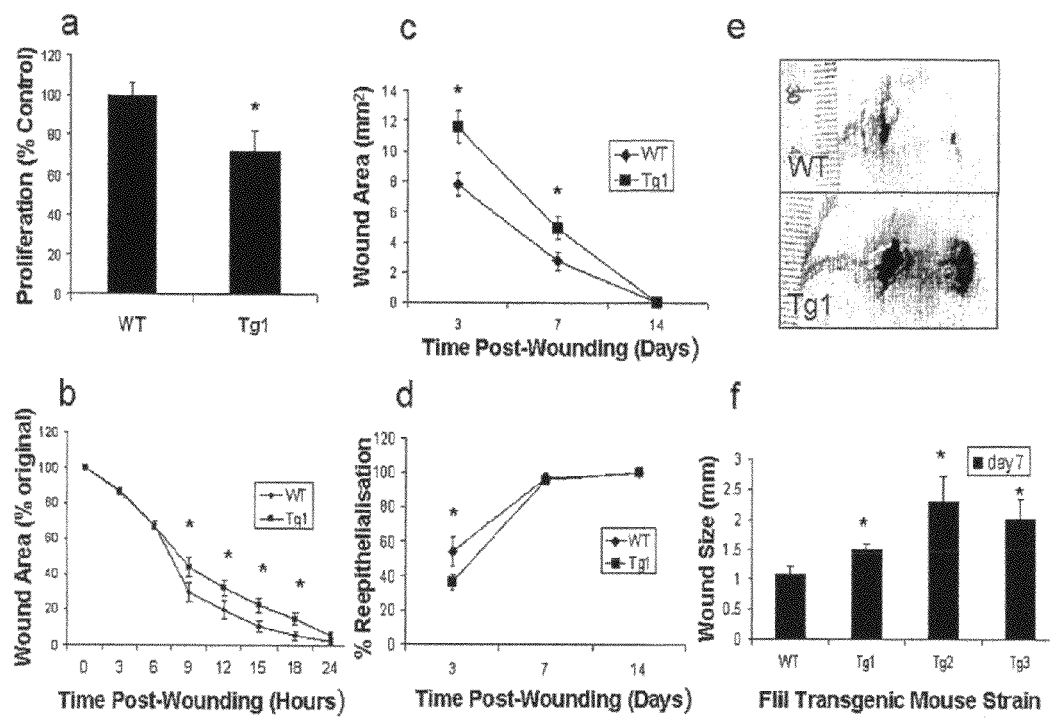
FIG. 3 shows that FliI overexpression decreases cell proliferation, reduces migration and impairs wound healing. (a) Primary fibroblasts derived from wild-type and FliI overexpressing (Tg1) mouse skins were cultured for 24 hours and their rates of proliferation determined (n=3, *P=0.017). (b) Primary fibroblasts derived from wild-type and FliI overexpressing mouse skin were cultured until confluent, scratch-wounded and the resultant wound area measured at various time-points post wounding. Results represent mean+/−s.e.m. (n=6, *P<0.05 vs equivalent wild-type time point). (c) Full thickness 1 cm incisions were made through the dorsal skin in wild-type (WT) and FliI transgenic (Tg1) mice. Macroscopic wound area measurements of WT and Tg1 wounds show that Tg1 wounds are significantly larger at day 7 compared to WT controls. *P=0.001 day 3 and 0.015 day 7 WT vs. Tg1. (d) Wound reepithelialisation was evaluated by measuring the percentage of the wound that had epidermal covering at day 3, 7, 14 and 21 (*P=0.025 day 3 WT vs. Tg1). (e) Representative day 7 wounds in WT and Tg1. (f) Size of wounds in WT, original transgenic mouse line (Tg1) and in two additional FliI overexpressing mouse lines (Tg2 and Tg3) at 7 days post-wounding. (n=4 for each group, *P values a=0.015, b=0.003, c=0.015 vs WT). (c-f) Results represent means+/−s.e.m. (n=12 for each group).

In an animal wound healing model, healing of incisional wounds created on FliI transgenic mice was severely delayed and wound areas were significantly larger than wild-type controls at 3 and 7 days post-wounding (P<0.015; FIG. 3c,e). Histological wound measurements of wound length and dermal gape confirmed this significant delay in wound closure (data not shown). Delayed reepithelialisation of the wounds was observed at 3 days post-wounding indicating a potential impairment in epidermal cell migration (P=0.02; FIG. 3d). An additional FliI transgenic line (Tg2) and an independent FliI transgenic line (Tg3) were also investigated. These mice were wounded and assessed 7 days post-injury (FIG. 3f). Healing was significantly impaired in all three FliI transgenic mice lines, with the wounds being larger than their wild-type controls (P<0.05). These results using Tg3 establish that the effect of transgenic overexpression of KU on wound healing is due to FliI itself and not to the position of chromosomal insertion of the transgene.

EXAMPLE 17

Figure 4:
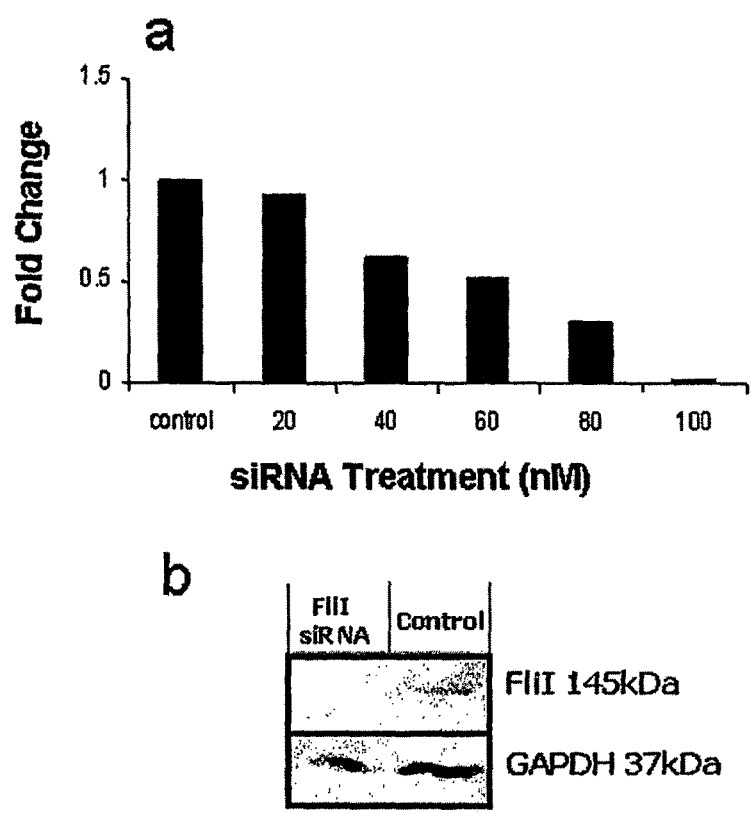
FIG. 4 shows that FliI siRNA reduces FliI gene and protein expression. RNA was extracted from human fibroblasts treated with increasing concentrations of FliI siRNA for 24 h. (a) Real-Time qPCR revealed decreased expression of FliI with increasing doses of siRNA. 100 nM siRNA was the most effective amount with an observed 98% decrease in nil gene expression. (b) Protein was extracted from human fibroblasts treated with 100 nM FliI siRNA for 24 hours and run on an acrylamide gel. Western Blot membranes were probed for FliI and GAPDH to assess loading. No FliI protein was observed in siRNA-treated fibroblasts.
Figure 5:
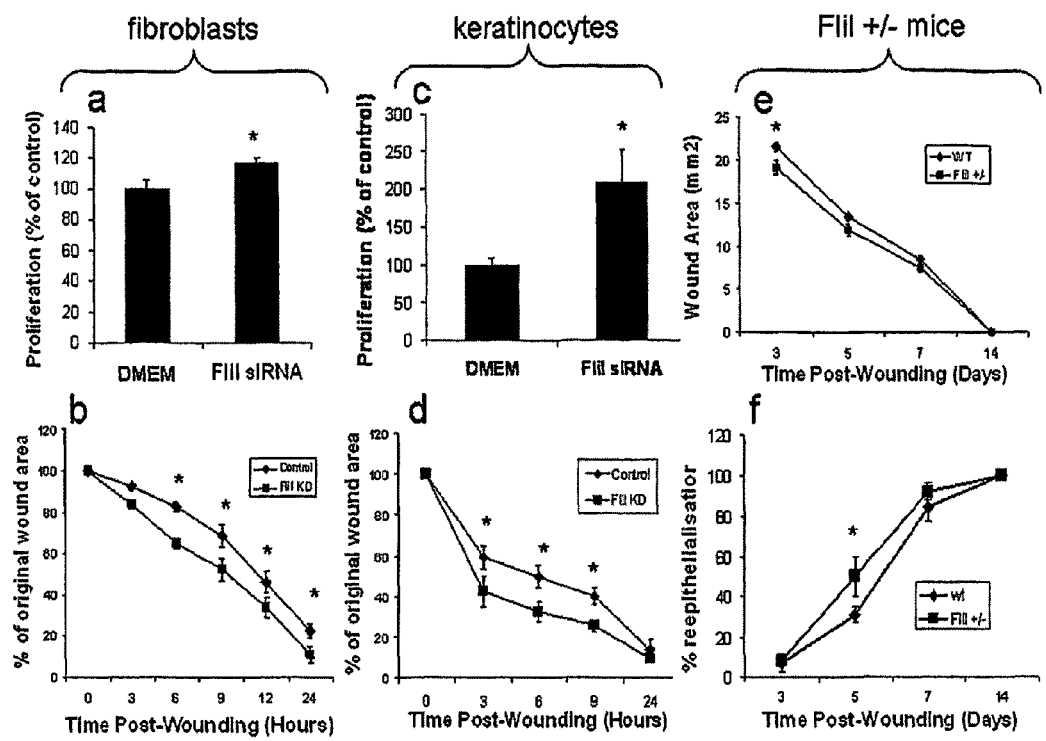
FIG. 5 shows that FliI deficiency increases cell proliferation, enhances migration and improves wound healing. Human fibroblasts were treated with FliI siRNA (100 nM) for 24 hours and the resulting effect on (a) cell proliferation and (b) migration determined using a WST-1 proliferation assay and a scratch wound assay respectively. Proliferation results represent mean+/−s.e.m. n=12 for each group, fibroblasts, *P=0.029 vs control. Scratch wound assay results represent mean+/−s.e.m n=9 for each group, *P<0.05 vs. equivalent control time-point. Keratinocytes were treated with FliI siRNA (60 nM. This being the optimal dose for FliI knockdown in keratinocytes, data not shown) for 24 hours and the resulting effect on (c) cell proliferation and (d) migration determined using a WST-1 proliferation assay and a scratch wound assay respectively. Proliferation results represent mean+/−s.e.m. n=12 for each group, fibroblasts, *P=0.021 vs control. Scratch Wound Assay results represent mean+/−s.e.m n=9 for each group, *P<0.05 vs equivalent control time point. Full thickness 1 cm$^2$ excisions were made through the dorsal skin in wild-type and FliI+/− mice. (e) Wound area was determined using planimetry measurements at 3, 5, 7 and 14 days post-wounding. Results represent means+/−s.e.m. (n=12 for each group, *P=0.011). (e) Wound reepithelialisation was evaluated by measuring the percentage of the wound that was covered by newly-formed epidermis at day 3, 5, 7, and 14. Results represent means+/−s.e.m. (n=12 for each group,*P=0.021).
Figure 6:
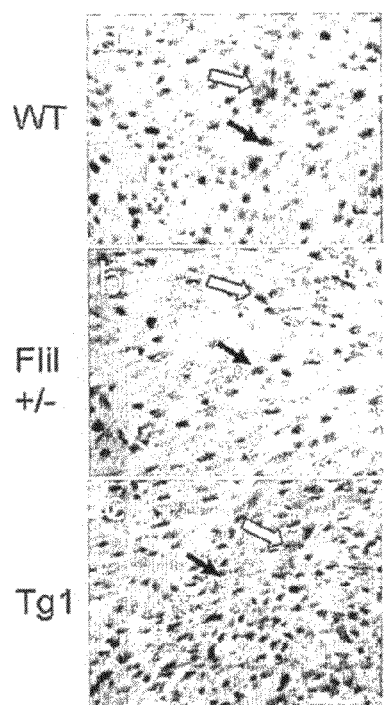
FIG. 6 shows that proliferation is impaired in FliI overexpressing wounds. (a-c) Wild-type (WT) FliI deficient (+/−) and FliI overexpressing (Tg1) day 7 wounds were stained for proliferating cell nuclear antigen (PCNA). Positive cells were counted in the wounds and expressed as a percentage of the total number of cells in this area (d). A significant decrease in proliferation was observed at day 3 in Tg1 wounds compared to wild-type and FliI+/− wounds. Results represent means+/−s.e.m. (n=6 for each group, *p<0.05). Scale bar in (c) refers to all images and =50 μm. Open arrows in (a-c) point to positive PCNA stained cells within the wounds. Closed arrows point to non-proliferating cells.
Figure 6:
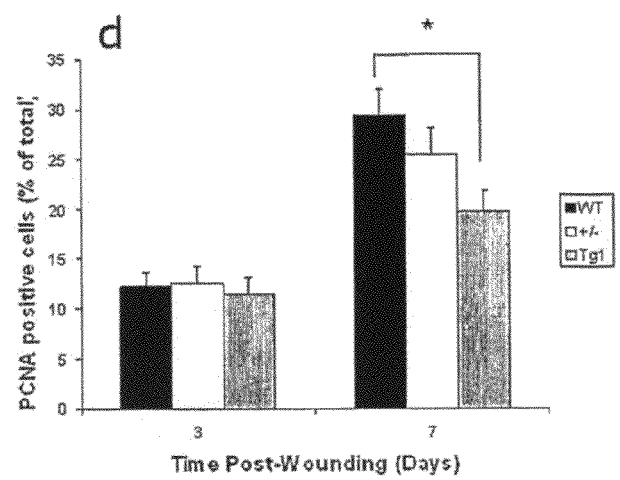

FliI Deficiency Increases Cell Proliferation, Enhances Migration and Improves Wound Healing To assess the functional role of FliI deficiency in skin fibroblasts and keratinocytes, siRNA was used to suppress FliI gene expression. FliI mRNA expression was reduced by over 90% in fibroblasts treated with 100 nM Flu siRNA for 24 hours (FIG. 4a). FliI protein levels were also greatly reduced following FliI siRNA treatment (FIG. 4b). The effect of reduced FliI expression on fibroblast proliferation was assessed and a significant increase was observed compared to controls (P=0.029 vs DMEM control, FIG. 5a). The effect of reduced FliI gene expression on cell migration was determined using a scratch wound assay. Confluent fibroblast monolayers, plus or minus FliI siRNA treatment, were scratch-wounded and the residual wound-area measured over 24 hours. The rate of cell migration was significantly increased (P<0.05 vs time-matched controls) in fibroblasts when Flit levels were reduced by siRNA (FIG. 5b). Decreased FliI gene expression using siRNA also significantly increased keratinocyte proliferation (P=0.021 vs DMEM control; FIG. 5c) and significantly increased the rate of migration (FIG. 5d).

The positive effect of FliI knockdown on key processes in wound healing in cultured skin cells was mirrored in FliI deficient+/− mice, with a significant improvement in wound healing being observed. Wound area measurements for the FliI+/− mice compared to wild-type controls were smaller at 3 and 7 days post-wounding although this was only statistically significant at 3 days when P=0.036 (FIG. 5e). The rate of reepithelialisation was significantly increased in FliL+/− mouse wounds with an approximate 20% increase in epithelial covering of the wound surface 5 days post injury (FIG. 5f). By 7 days, reepithelialisation of the wild-type wounds was no longer significantly different from the Fli+/− wounds reflecting the inherent capacity of mouse skin to heal. Although these improvements were modest, this may reflect that these mice are only heterozygous knockout and it might be expected that an even greater improvement in healing would be observed if FliI levels were reduced further.

EXAMPLE 18

Proliferation is Impaired in FliI Overexpressing Wounds

The effect of altered FliI levels on cell proliferation in vivo was investigated in wounds from wild-type, FliI deficient+/− and FliI overexpressing (Tg1) mice. PCNA positive cells were counted within the migrating tongue of the epidermis at the wound edge and within the dermal wound bed. No differences were observed in proliferating cells within the epidermis (data not shown) but significantly fewer proliferating cells were observed within the dermis of FliI overexpressing wounds at 7 days post-wounding compared to their wild-type counterparts (FIG. 6a-d).

EXAMPLE 19

Exogenous Addition of FliL Antibodies Accelerates Wound Healing

Figure 7:
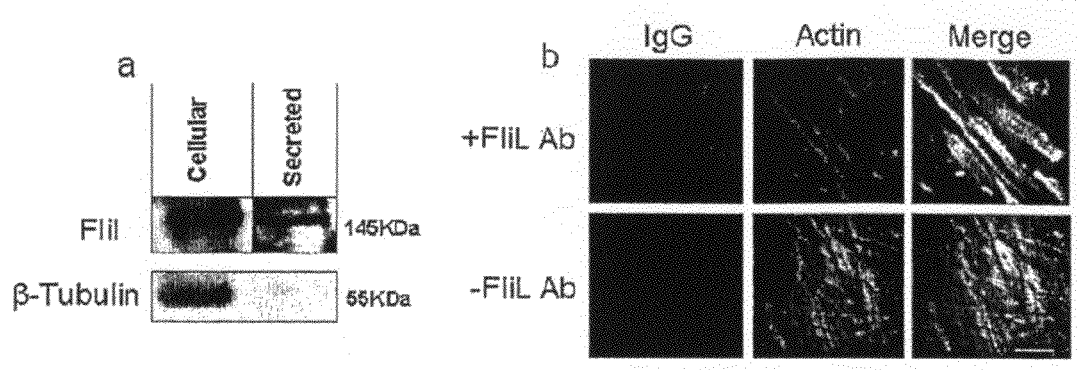
FIG. 7 shows that FliI neutralising antibodies increase fibroblast proliferation. Fibroblasts were scratch-wounded and after 24 hours conditioned medium collected. (a) Cells were lysed and the soluble cellular fraction and the conditioned medium separated by SDS-PAGE, immunoblotted and probed with antibodies to FliI and β-tubulin. (b) Fibroblasts were grown on coverslips and incubated with or without FliI neutralising antibody for 24 hours. The cells were incubated with a biotinylated anti-rabbit secondary antibody and subsequently with streptavidin-CY3 to visualise FliI antibody and FITC-Phalloidin to visualise the actin filaments. Images are representative images from 3 independent experiments.
Figure 8:
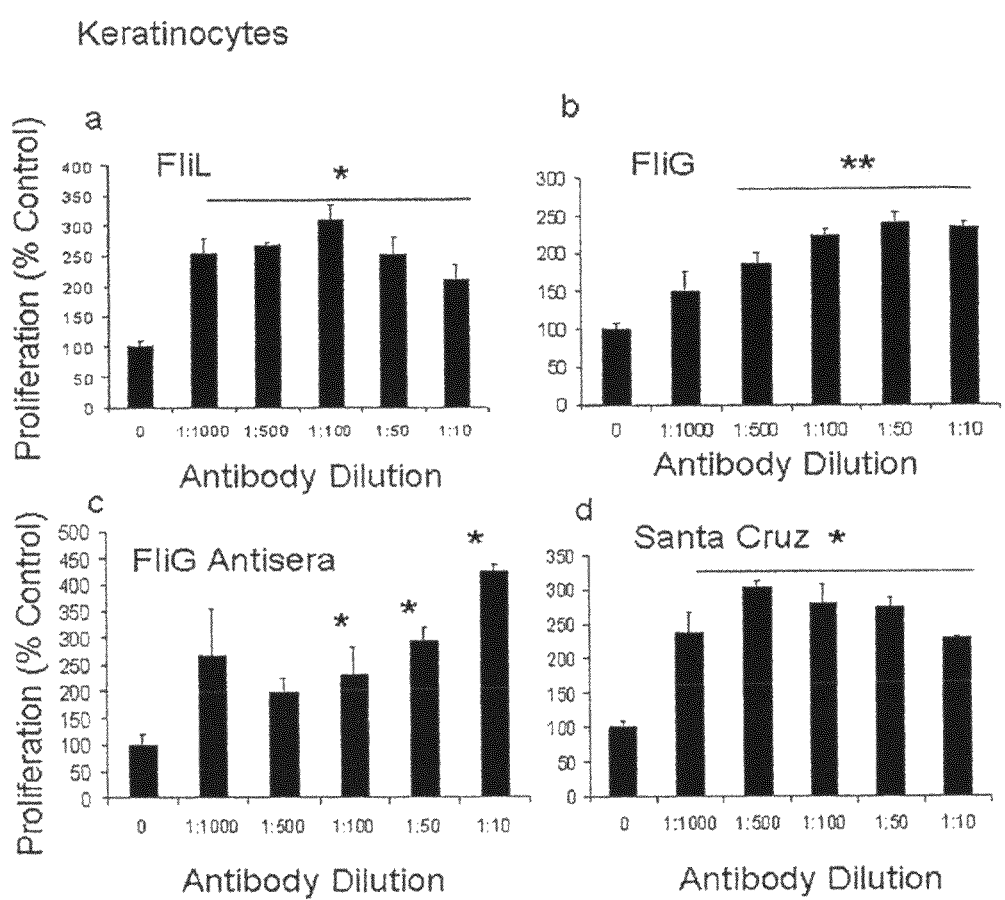
FIG. 8 shows the effect of FliI Antibodies on human keratinocytes. Human keratinocytes (HaCats) were incubated with increasing concentrations of FliI neutralizing antibodies (a) FliL, (b) FliG, (c) FliG antisera, (d) FliI antibody from Santa-Cruz (Calif.). The effect on cell proliferation was determined using the WST-1 proliferation Assay (Roche). Results represent means+/−s.e.m. (n=12 for each group, *<0.05).

To test whether FliI is also secreted we concentrated conditioned medium and cell lysate from skin fibroblasts, previously scratch wounded to maximise FliI expression, and electrophored these samples using SDS-PAGE and immunoblotted for FliI and β-tubulin. A band corresponding to FliI was observed in both conditioned medium and cell lysate (FIG. 7a), whereas β-tubulin was only detected in the cell lysate and not in the conditioned medium, suggesting that FliI is secreted and its presence in the medium is not due to an artefact of the in vitro culture (FIG. 7a).

Given the positive effects of reduction of FliI on wound healing in vitro and in vivo by RNA knockdown or gene inactivation in heterozygous knockout mice, we next explored whether we could use FliI antibodies to block FliI activity to achieve the same effect. An affinity purified antibody raised against the leucine rich repeat domain of the FliI protein (FliL) was investigated for its ability to neutralise FliI activity in vitro. As clearly not all FliI is secreted in response to injury (FIG. 1) we first seeded fibroblasts onto coverslips and treated them plus or minus FliL antibody for 24 hours. Immunocytochemistry was performed minus primary antibody using biotinylated Rabbit IgG and immunofluorescence localisation (FIG. 7b). Confocal microscopy confirmed that the FliL antibody had entered the cells, as positive staining for FliL was observed in the cytoplasm of antibody treated but not control cultures.

EXAMPLE 20

Effect of FliI Antibodies on Cell Proliferation

Figure 9:
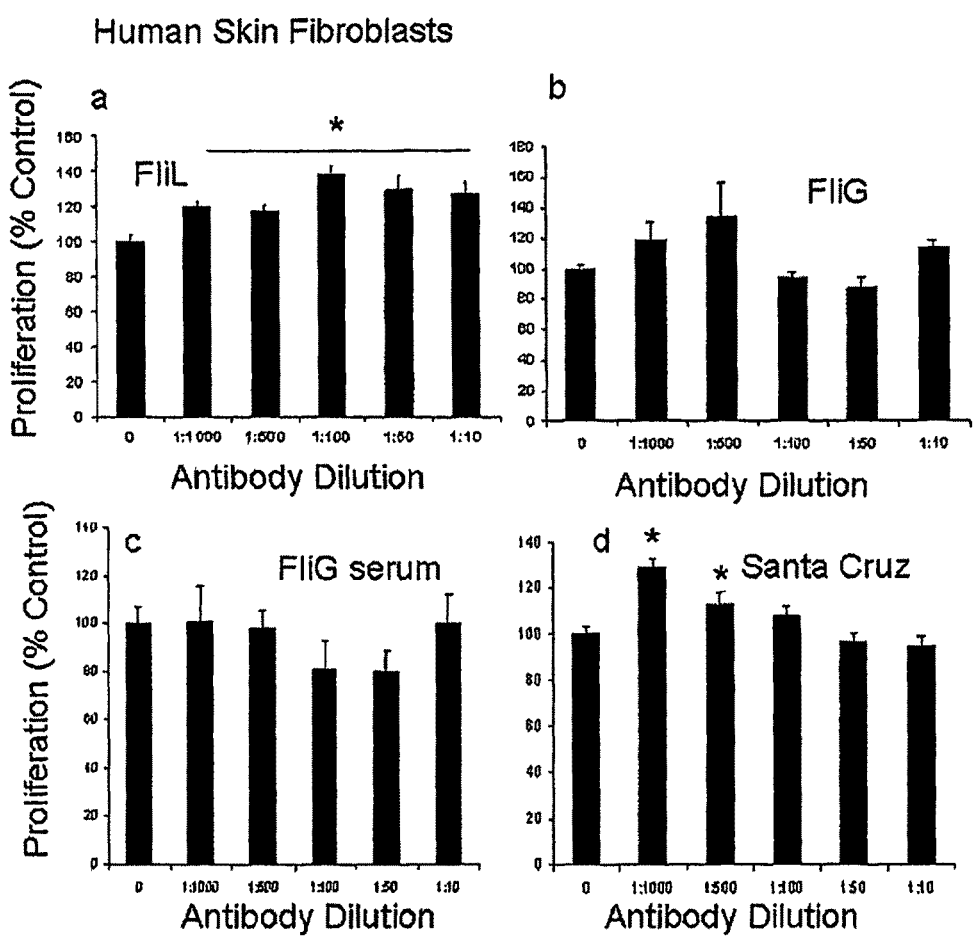
FIG. 9 shows the effect of FliI Antibodies on human skin fibroblasts. Human skin fibroblasts were incubated with increasing concentrations of FliI neutralizing antibodies (a) FliL, (b) FliG, (c) FliG antisera, (d) FliI antibody from Santa-Cruz (CA). The effect on cell proliferation was determined using the WST-1 proliferation Assay (Roche). Results represent means+/−s.e.m. (n=12 for each group, *<0.05).
Figure 10:
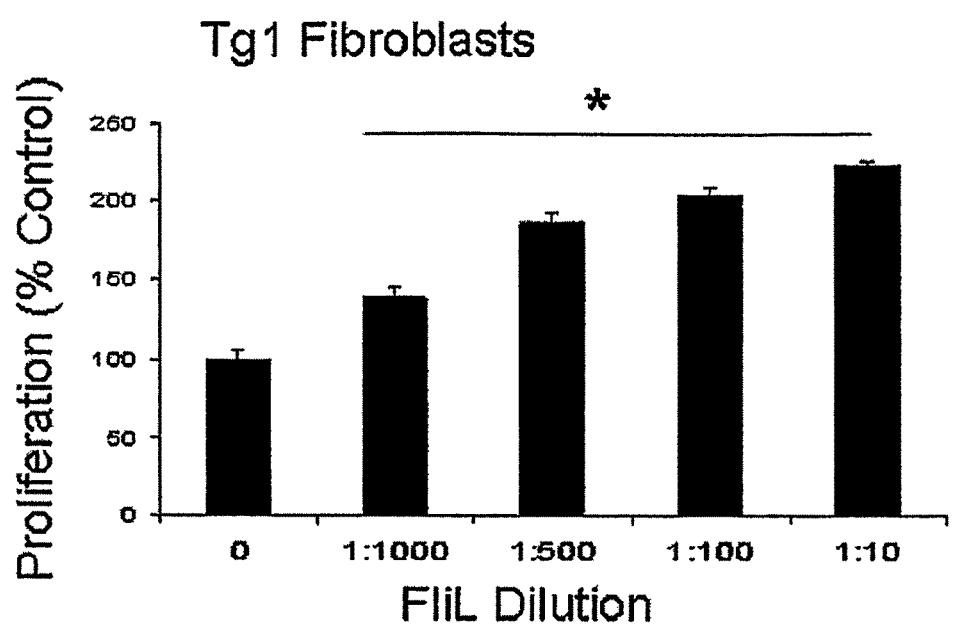
FIG. 10 shows the effect of FliL Antibody on FliI overexpressing skin fibroblasts. Primary skin fibroblasts cultured from FliI overexpressing skin were incubated with increasing concentrations of FliI neutralizing antibody FliL. The effect on cell proliferation was determined using the WST-1 proliferation Assay (Roche). Results represent means+/−s.e.m. (n=12 for each group, *<0.05).

All the FliI antibodies investigated significantly increased human keratinocyte cell proliferation particularly at the higher doses (FIG. 8a-d). In contrast, the effect of FliI antibodies on human skin fibroblasts was less dramatic, with only FliL and the commercial Santa Cruz antibody showing significant effects on proliferation (FIG. 9a and d respectively). To determine whether FliI antibodies could neutralize FliI in fibroblasts derived from FliI overexpressing mice skin, FliL was added in increasing concentrations and a significant increase in cell proliferation was observed above that was observed for normal fibroblasts (FIG. 10). As FliI was the optimal antibody for neutralizing FliI in both keratinocytes and fibroblasts this antibody was chosen for application to in vivo incisional wounds.

This method also demonstrates the general concept of being able to screen for agents that modulate wound repair.

EXAMPLE 21

Exogenous Addition of FliL Antibodies Accelerates Wound Healing In Vivo

Figure 11:
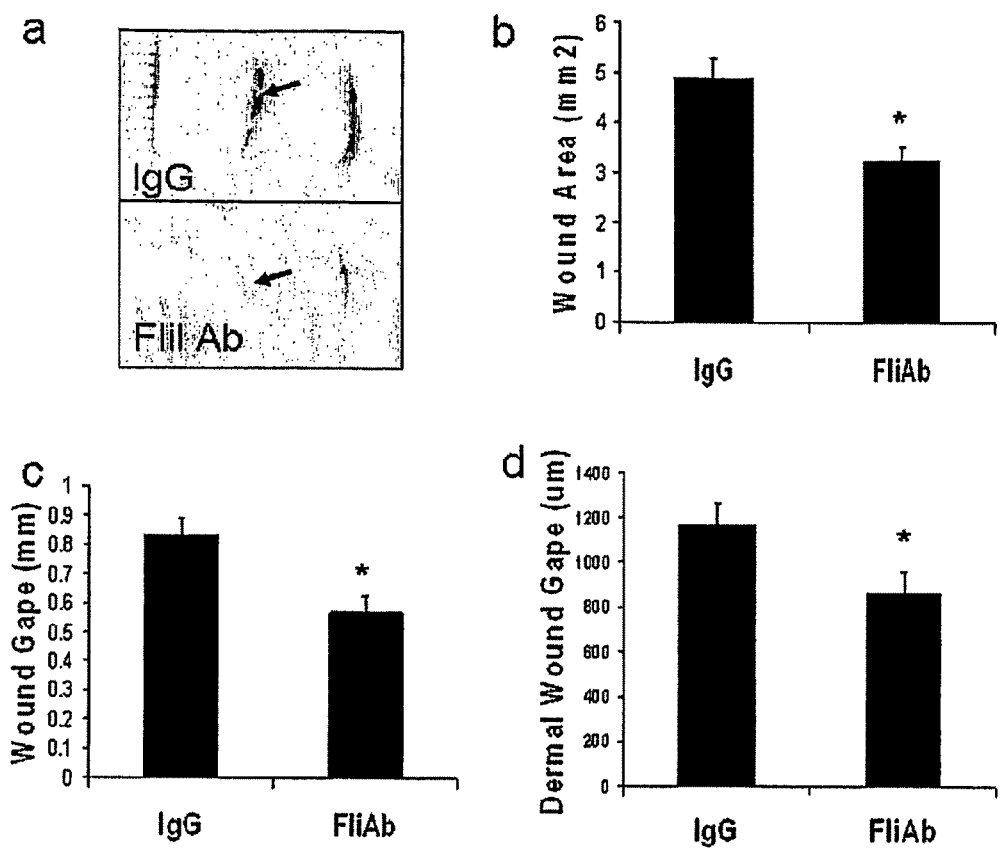
FIG. 11 shows that exogenous addition of FliI neutralising antibodies accelerates wound healing. Incisional wounds in wild-type mice were injected with FliI neutralising antibodies or equivalent dose of rabbit IgG. Wounds 7 days after treatment are shown in (a). The wound area (b) and wound gape (c) were measured. (d) Histological measurement of the distance between the dermal wound edges. Results represent mean+/−s.e.m. (n=10 for each group, *P<0.05).

To test whether FliI antibodies could have a beneficial effect on wound healing in vivo, FliL antibody or dose-matched rabbit IgG were next injected intradermally around incisional wounds of wild-type mice and the effect on wound healing determined after 7 days (FIG. 11a). Macroscopic analysis revealed that treatment with FliL had decreased the wound area and wound gape by 33% and 31% respectively compared to IgG treated controls. (FIG. 11b,c) Similarly, microscopic analysis of the wounds confirmed that treatment of the wounds with the FliI neutralising antibody significantly decreased the distance between the dermal wound margins (P=0.047, FIG. 11d).

EXAMPLE 22

Figure 12:
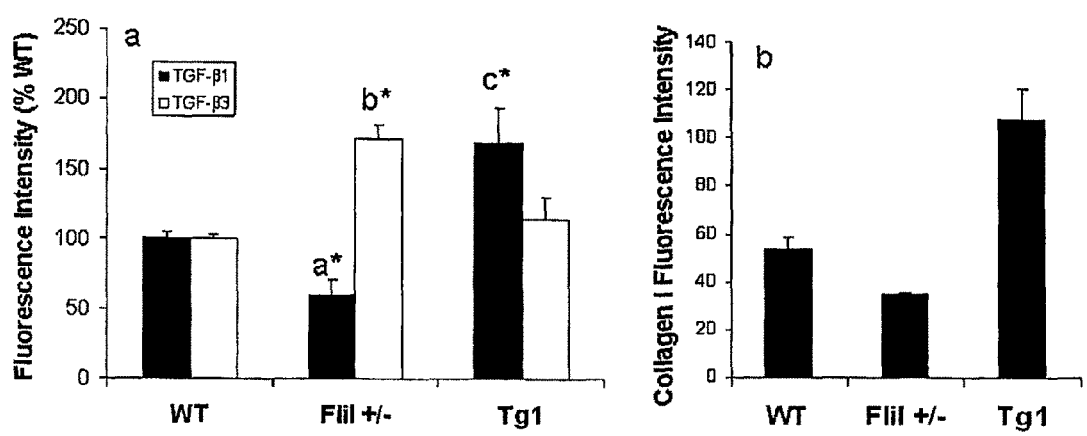
FIG. 12 shows differential expression of FliI affects TGF-β and collagen I expression in wounds. Wounds from wild-type (WT), FliI deficient+/− (+/−) and FliI transgenic (Tg1) mice were immunostained for TGF-β1, TGF-β3 and collagen I. (a) Immunofluorescence intensity of TGF-β1 and TGF-β3 at 7 days post-wounding. (b) Fluorescence intensity of collagen I at 14 days post-wounding. * denotes significance and P<0.05. Results represent means+/−s.e.m. n=12 for each group.

Differential Expression of FliI Affects TGF-β and Collagen I Expression in Wounds To determine if TGF-β1, TGF-β3 and collagen I were affected by differential expression of FliI in wound repair, wounds created in wild-type, FliI deficient+/− and FliI overexpressing mice were subjected to immunohistochemistry and the resulting staining patterns quantified (FIG. 12a). Significantly reduced levels of TGF-β1 were observed in FliI deficient+/− wounds at 7 days post-wounding compared to wild-type (P=0.022; FIG. 12a). In marked contrast, significantly increased staining for TGF-β3 was observed in FliI deficient wounds (P=0.008; FIG. 12a). TGF-β1 was significantly elevated in FliI overexpressing wounds with little effect of FliI overexpression being observed on TGF-β3 (FIG. 12a). Reduced collagen I expression was also observed in FliI deficient wounds at 14 days post wounding (P=0.023; FIG. 12b) and elevated collagen I was observed in FliI transgenic wounds (P=0.013; FIG. 12b). No effect of differential FliI gene expression was observed on collagen III at any time-point post-wounding (data not shown).

Discussion

The actions of members of the gelsolin family of actin-severing proteins are essential for remodelling the actin cytoskeleton yet their function in wound repair is poorly understood. The present study demonstrates that the actin-remodelling protein FliI is an important regulator of wound repair, affecting both cell proliferation and motility. We studied the effect of FliI deficiency in mice heterozygous for the FliI gene knockout, since homozygous deletion of FliI is embryonic lethal. In mice heterozygous for the FliI gene knockout, healing is enhanced as evidenced by the reduction in wound size compared to wild-type controls and the increased rate of re-epithelialisation. In contrast, wounds in mice overexpressing FliI heal significantly slower, with delayed reepithelialisation. Three independent lines of FliI overexpressing mice were used in this study and all three showed significant impairments in wound repair confirming that FliI overexpression and not just the position of the chromosomal insertion of the transgene was causing the observed differences. The improvement in wound healing in FliI heterozygous null mice was modest, most likely reflecting the presence of one remaining functional FliI allele. However, it was statistically significant and it indicated the potential benefits in being able to reduce FliI expression.

FliI localises to β-tubulin-based structures known to be involved in cell division suggesting a role for FliI in cell proliferation processes. Quantification of the number of proliferating dermal cells within the wounds revealed significantly fewer proliferating cells in the FliI overexpressing mice wounds compared to wild type wounds. This deficiency in dermal cell proliferation within the wound bed is likely to contribute to the observed impaired healing. Interestingly, no significant difference was observed in the number of proliferating dermal cells in the FliI+/− wounds, perhaps also reflective of the remaining functional FliI allele within the cells. Our in vitro data support our in vivo studies, revealing that reduced FliI gene expression increases both fibroblast and keratinocyte motility and proliferation. In contrast, fibroblasts overexpressing FliI show reduced migration and proliferation which is likely to contribute to the observed impaired healing phenotype. Our studies confirm that FliI is involved in both cell proliferation and migration and that it may negatively regulate these processes, perhaps via its actin severing abilities.

Our in vitro studies showed that an affinity purified antibody raised against the Leucine Rich Repeat domain of the FliI protein has significant effects on both keratinocyte and fibroblast cell proliferation, with increased numbers of cells being observed following treatment with increasing doses of FliL antibody. Our studies have revealed cytoplasmic, but not nuclear, staining of FliL following addition of the antibody to fibroblasts in culture, indicating that FliL is able to penetrate the cell membrane. Whether this is by binding to Fc receptors and subsequent internalisation or by binding to a specific FliI receptor has still to be determined. Although FliL was thought to be solely an intracellular protein we now have new evidence which shows that it is also secreted by fibroblasts in culture. Intradermal application of FliL antibody to incisional wounds significantly reduces the size of these wounds at 7 days post-injury. Therefore, FliL represents a potential effective novel therapeutic factor to improve impaired wound healing.

Our studies also show that wounds in FliI deficient mice have reduced TGF-β1 yet increased expression of TGF-β3 and that these wounds have improved healing.

In summary, our data have revealed that FliI is an important regulator of cell proliferation, migration and wound repair. Topical application of FliI antibodies to incisional wounds significantly enhances wounds repair. Therefore manipulation of FliI levels may lead to potential new therapeutic interventions by which wound healing may be improved.

Finally, it will be appreciated that various modifications and variations of the methods and compositions of the invention described herein will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are apparent to those skilled in the field of molecular biology or related fields are intended to be within the scope of the present invention.

The invention claimed is:

1. A method of improving repair of a skin wound in a subject, the method including administering to the subject an effective amount of an agent that decreases activity of Flightless I in one or more cells of the subject involved in repair of the wound to thereby improve repair of the wound, wherein the agent is a neutralizing antibody to Flightless I, or an antigen binding part of a neutralizing antibody to Flightless I.

2. A method according to claim 1, wherein the agent is a neutralising antibody to Flightless I, or an antigen binding part thereof.

3. A method according to claim 1, wherein the agent is delivered to the wound by administration of the agent to the wound and/or a region near the wound.

4. A method of reducing scar formation in a skin wound of a subject, the method including the step of delivering to the wound an effective amount of an agent that decreases activity of Flightless I and thereby reduces scar formation in the wound, wherein the agent is a neutralizing antibody to Flightless I, or an antigen binding part of a neutralizing antibody to Flightless I.

5. A method of decreasing one or more of expression, secretion and/or activity of TGF-β1 and/or decreasing secretion of collagen I in a cell of a subject, the method including administering to the subject an agent to decrease activity of Flightless I in the cell to thereby decrease one or more of expression, secretion and/or activity of TGF-β1 and/or decrease secretion of collagen I in the cell, wherein the agent is a neutralizing antibody to Flightless I, or an antigen binding part of a neutralizing antibody to Flightless I, and wherein the cell is a cell involved in skin wound repair and/or scar formation in a skin wound.

6. A method according to claim 5, wherein the cell is a fibroblast or a keratinocyte.

7. A method of increasing migration and/or proliferation of a cell involved in skin wound repair or scar formation in a skin wound in a subject, the method including delivering an effective amount of an agent that decreases activity of Flightless I to cells in the subject involved in repair of the wound or scar formation to thereby increase migration and/or proliferation of the cell, wherein the agent is a neutralizing antibody to Flightless I, or an antigen binding part of a neutralizing antibody to Flightless I.

8. A method according to 7, wherein the cell is a fibroblast or a keratinocyte.

9. A method according to claim 7, wherein the agent is a neutralizing antibody to Flightless I or an antigen binding portion thereof.

* * * * *

SEQUENCE LISTING

```
<160> NUMBER OF SEQ ID NOS: 4

<210> SEQ ID NO 1
<211> LENGTH: 26
<212> TYPE: DNA
<213> ORGANISM: Artificial
<220> FEATURE:
<223> OTHER INFORMATION: primer sequence

<400> SEQUENCE: 1
cctcctacag ctagcaggtt atcaac                                          26

<210> SEQ ID NO 2
<211> LENGTH: 26
<212> TYPE: DNA
<213> ORGANISM: Artificial
<220> FEATURE:
<223> OTHER INFORMATION: primer sequence

<400> SEQUENCE: 2
gcatgtgctg gatatatacc tggcag                                          26

<210> SEQ ID NO 3
<211> LENGTH: 20
<212> TYPE: DNA
<213> ORGANISM: Artificial
<220> FEATURE:
<223> OTHER INFORMATION: primer sequence

<400> SEQUENCE: 3
```

```
ggttggatgg caagcatgtg                                            20

<210> SEQ ID NO 4
<211> LENGTH: 20
<212> TYPE: DNA
<213> ORGANISM: Artificial
<220> FEATURE:
<223> OTHER INFORMATION: primer sequence

<400> SEQUENCE: 4
tgctggtctt gccattcctg                                            20
```